US011693005B2

(12) United States Patent
Blakely et al.

(10) Patent No.: US 11,693,005 B2
(45) Date of Patent: Jul. 4, 2023

(54) METHODS FOR IDENTIFYING TREATMENTS THAT REDUCE THE ACTIONS OF SUBSTANCES OF ABUSE AND ADDICTION

(71) Applicant: Florida Atlantic University Board of Trustees, Boca Raton, FL (US)

(72) Inventors: Randy D. Blakely, West Palm Beach, FL (US); Maureen K. Hahn, Jupiter, FL (US)

(73) Assignees: FLORIDA ATLANTIC UNIVERSITY BOARD OF TRUSTEES, Boca Raton, FL (US); VANDERBILT UNIVERSITY, Nashville, TN (US)

( * ) Notice: Subject to any disclaimer, the term of this patent is extended or adjusted under 35 U.S.C. 154(b) by 483 days.

(21) Appl. No.: 16/056,988

(22) Filed: Aug. 7, 2018

(65) Prior Publication Data

US 2020/0049711 A1  Feb. 13, 2020

(51) Int. Cl.
 *G01N 33/573* (2006.01)
 *A61K 49/00* (2006.01)
 *G01N 33/50* (2006.01)

(52) U.S. Cl.
 CPC ....... *G01N 33/573* (2013.01); *A61K 49/0008* (2013.01); *G01N 33/5023* (2013.01); *G01N 2333/986* (2013.01)

(58) Field of Classification Search
 CPC ............. G01N 33/573; G01N 33/5023; G01N 2333/986; A61K 49/0008
 See application file for complete search history.

(56) References Cited

U.S. PATENT DOCUMENTS

| | | | |
|---|---|---|---|
| 6,201,168 | B1 | 3/2001 | Campbell et al. |
| 7,005,255 | B2 | 2/2006 | Kaddurah-Daouk et al. |
| 7,294,637 | B2 * | 11/2007 | Aquila ............... C07D 401/06 514/317 |
| 9,977,034 | B2 | 5/2018 | McCreedy et al. |

OTHER PUBLICATIONS

Retzlaff et al., Neuropsychopharmacology, 41: S116-S288, 2016, pp. S116 and S214 only, Abstract M152. (Year: 2016).*
Pitlik et al., Bioorganic and Medicinal Chemistry Letters, 7(24): 3129-3134, 1997. (Year: 1997).*
Tahlan et al., The Journal of Antibiotics, 66:401-410, 2013. (Year: 2013).*
Hardaway et al.: "Glial Expression of the Caenorhabditis elegans Gene swip-10 Supports Glutamate Dependent Control of Extrasynaptic Dopamine Signaling", The Journal of Neuroscience, Jun. 24, 2015• 35(25) 9409-9423 • 9409.
Retzlaff et al.: "Metallo-ß-lactamase Domain-Containing Protein 1 (MBLAC1) is a Specifc, High-Affinity Target for the Glutamate Transporter Inducer Ceftriaxone", ACS Chem, Neursci. 2017, 8, 2132-2138.
Rao et. al.: "Designing Novel Nanoformulations Targeting Glutamate Transporter Excitatory Amino Acid Transporter 2: Implications in Treating Drug Addiction", J Pers Nanomed. 2015; 1 (1): 3-9.
Lewerenz et al.: "Induction of Nrf2 and xCT are involved in the action of the neuroprotective antibiotic ceftriaxone in vitro", Journal of Neurochemistry, 2009, 111, 332-343.
Hardaway et al.: "Forward Genetic Analysis to Identify Determinants of Dopamine Signaling in Caenorhabditis elegans Using Swimming-Induced Paralysis", G3 Genes Genomes Genetics, vol. 2, Aug. 2012.
Tallarida et. al.: "Ceftriaxone attenuates locomotor activity induced by acute and repeated cocaine exposure in mice", Neurosci Lett. Nov. 27, 2013; 556: 155-159.
Roberts-Wolfe et. al.: "Glutamate transporter GLT-1 as a therapeutic target for substance use disorders", CNS Neurol Disord Drug Targets. 2015 ; 14(6): 745-756.
Sari et al.: "Up-regulation of GLT1 attenuates cue-induced reinstatement of cocaine-seeking behavior in rats" J Neurosci. Jul. 22, 2009; 29(29): 9239-9243.
Knackstedt et al.: "Ceftriaxone restores glutamate homeostasis and prevents relapse to cocaine-seeking" Biol Psychiatry. Jan. 1, 2010; 67(1): 81-84.
Rawls et al.: "ß-lactam antibiotic inhibits development of morphine physical dependence in rats" Behav Pharmacol. Mar. 2010; 21(2): 161-164.
Ward et al.: "ß-lactam antibiotic decreases acquisition of and motivation to respond for cocaine, but not sweet food, in C57Bl/6 mice," Behav Pharmacol. Aug. 2011; 22(4): 370-373.
Bell et. al.: "Rat animal models for screening medications to treat alcohol use disorders," Neuropharmacology. Aug. 1, 2017; 122: 201-243.
Gibson et. al.: "Global untargeted serum metabolomic analyses nominate metabolic pathways responsive to loss of expression of the orphan metallo b-lactamase, MBLAC1", Mol. Omics, 2018, 14, 142-155.
Rothstein et al.: "ß-Lactam antibiotics offer neuroprotection by increasing glutamate transporter expression", Nature, vol. 433, Jan. 6, 2005.

(Continued)

Primary Examiner — Teresa E Knight
(74) Attorney, Agent, or Firm — Fox Rothschild LLP

(57) ABSTRACT

Based on the discovery that MBLAC1 is a specific, high-affinity target for Ceftriaxone (Cef), MBLAC1 may be used for identifying treatments for addiction to substances of abuse. Methods for identifying therapeutic agents for treatment of addiction to a substance of abuse include using an assay to determine if a test agent is capable of binding to MBLAC1 or disrupting binding between MBLAC1 protein and Cef, and identifying such a test agent as a candidate therapeutic agent for treatment of addiction to a substance of abuse. MBLAC knock-out (KO) animals, methods of use thereof, and kits are used for identifying a therapeutic agent that reduces the actions of at least one substance of abuse. Methods also include using cellular extracts from tissue or cultured cells taken from wild-type (WT) MBLAC1 and MBLAC1 KO animals for screening for novel, Cef-like molecules in vitro, and using cells from a MBLAC1 KO animal to test for Cef-like actions of a test molecule.

10 Claims, 7 Drawing Sheets

Specification includes a Sequence Listing.

(56) References Cited

OTHER PUBLICATIONS

Hsu et al. Nat Biotechnology. Sep.;31 (9):827-32 (Year: 2013).
Lee et al. Drug Discovery Today: Disease Models, vol. 20, p. 13-20 (Year: 2016).
Guo et al. Cell Research, vol. 25, p. 767-768 (Year: 2015).
Yang et al., PNAS, 113(41), E6209-E6218, 1-10 (Year: 2016).
Caldwell et al., "Can Untargeted Metabolomics be Utilized in Drug Discovery/Development", Current Topics in Medicinal Chemisitry, 2017, 17, pp. 2716-2739.
Ramautar et al., "Human metabolomics strategies to understand biology", Current Opinion in Chemical Biology, 2013, 17, pp. 841-846.
Mangalam et al., "Profile of Cicrulatory Metabolites in a Relapsing-remitting Animal Model of Multiple Sclerosis using Global Metabolomics", J Clin Cell Immunol., Jun. 30, 2013.
Rattray, "Environmental influences in the etiology of colorectal cancer: the premise of metabolomics", Curr Mangalam et al., "Profile of Cicrulatory Metabolites in a Relapsing-remitting Animal Model of Multiple Sclerosis using Global Metabolomics", J Clin Cell Immunol., Jun. 30, 2013.
NCBI accession No. NM_177878.3. pp. 1-2 (Year: 2014).
Shen et al., Cell Res vol. 23, 720-723 (Year: 2013).
Boettcher Mol Cell. May 21; 58(4): 575-585, p. 1-24. (Year: 2015).
Patil et al. Indian Journal of Public Health research & Development. vol. 2, No. 1, p. 106-109 (Year: 2011).
Khodarovich et al. Applied Biochemistry and Microbiology, vol. 49, No. 9, 711-722 (Year: 2013).
Selsby et al. ILARJoumal, vol. 56, No. 1, p. 116-126 (Year: 2015).
Maksimenko et al. Acta Naturae, vol. 5, No. 1, p. 33-46 (Year: 2013).

\* cited by examiner

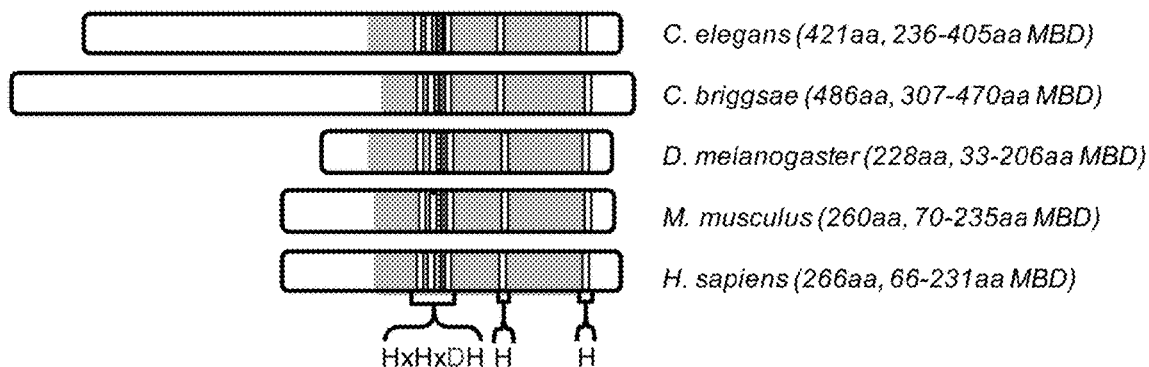
FIG. 1A
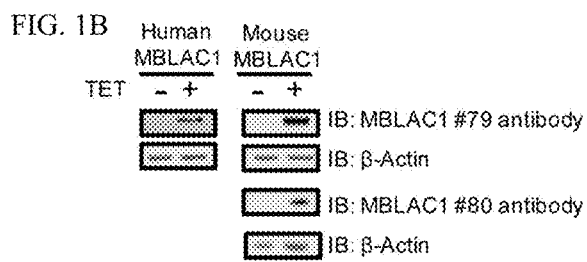
FIG. 1B
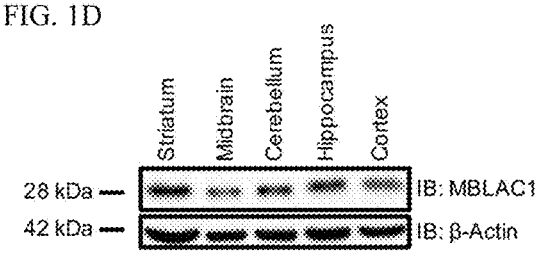
FIG. 1D
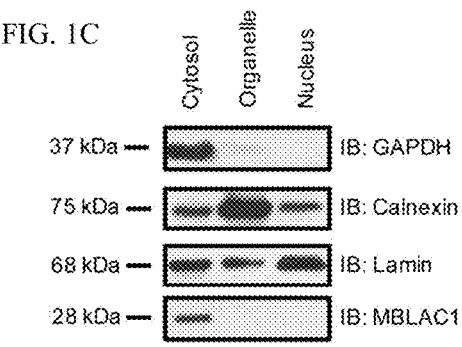
FIG. 1C
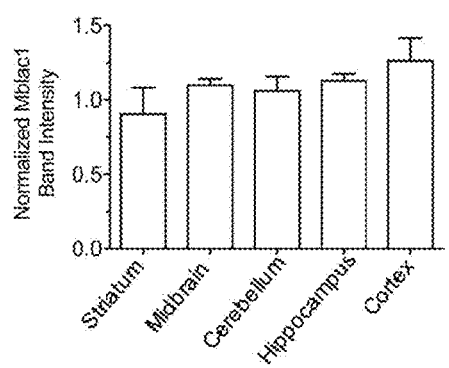

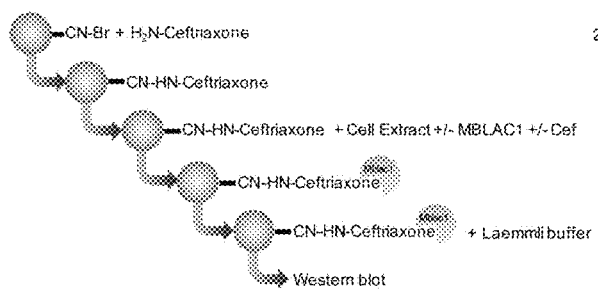
FIG. 2A
FIG. 2B
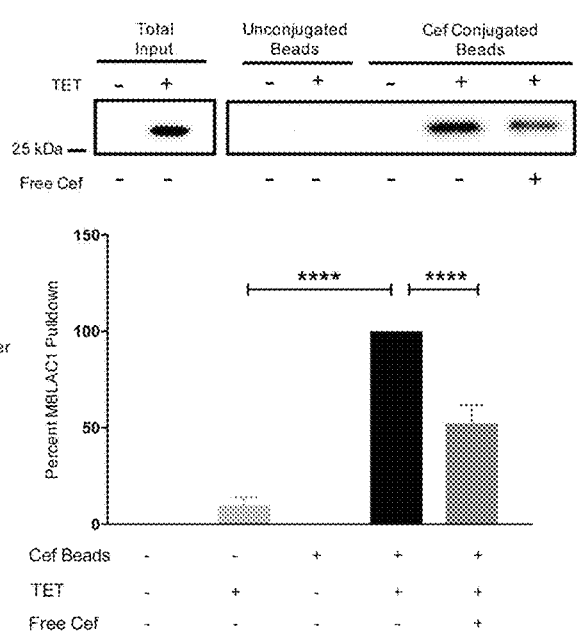
FIG. 2C

FIG. 4A, FIG. 4B, FIG. 4C, FIG. 4D

METHODS FOR IDENTIFYING TREATMENTS THAT REDUCE THE ACTIONS OF SUBSTANCES OF ABUSE AND ADDICTION

FIELD OF THE INVENTION

The invention relates generally to the fields of pharmacology, medicine, neurology and psychiatry. In particular, the invention relates to methods for identifying therapeutic agents for treating addiction and substance abuse in a mammal.

CROSS-REFERENCE TO A SEQUENCE LISTING

This application includes a "Sequence Listing" which is provided as an electronic document having the file name "6818-318_ST25.txt" (8,037 bytes, created Aug. 7, 2018), which is herein incorporated by reference in its entirety.

BACKGROUND

Molecules bearing a four-membered β-lactam ring, typified by penicillin and the cephalosporins, are widely prescribed antibiotics (Van Boeckel et al., Lancet Infect Dis 14: 742-750, 2014). By interfering with cell wall synthesis, these agents halt bacterial cell division unless inactivated by β-lactamase proteins. Studies over the past decade have revealed that a number of these agents exhibit central nervous system (CNS) actions independent of their antimicrobial actions. One such study (Rothstein et al., Nature 433: 73-77, 2005), seeking opportunities to repurpose FDA-approved medications for the treatment of Amyotrophic Lateral Sclerosis (ALS), identified β-lactam antibiotics as candidates based on their ability to elevate expression of the glutamate (Glu) transporter, GLT-1. In particular, ceftriaxone (Cef), a CNS penetrant, cephalosporin-type, β-lactam antibiotic, showed high-potency in these studies. Subsequently, multiple groups have demonstrated Cef actions in a range of neurological and neurobehavioral disease models, including those for stroke, epilepsy, Parkinson's disease, and addiction, paralleled by normalization of pathological elevations in synaptic Glu levels. Cef has also been reported to elevate expression of the glial cystine/Glu exchanger (Xc−), thereby also normalizing extrasynaptic Glu levels. At present, the in vivo pharmacokinetics of existing inducers of GLT-1 such as Cef are poor (Rao et al., J Pers Nanomed 1(1):3-9, 2015), and the CNS target responsible for Cef action until recently was unknown.

SUMMARY

In the experiments described below, Cef's brain target was identified, and understanding Cefs brain target now provides opportunities to develop new therapeutics for the many disorders attributed to Glu dysfunction, including addiction. Cef, a β-lactam antibiotic, has been reported to act independently of its antimicrobial actions to normalize perturbed CNS glutamate levels, principally by elevating expression of glial glutamate transporters. The experiments described below were driven by the hypothesis that identification of a specific, high-affinity target for Cef would significantly impact therapeutic development for multiple brain disorders, ranging from neurodegenerative disorders to addiction. Previously, a glial-expressed *C. elegans* gene, swip-10, was identified, that encodes a metallo-β-lactamase domain (MBD)-containing protein, and limits glutamate-dependent changes in dopamine neuron excitability. Bioinformatic analyses identified Mblac1 as the likely mammalian ortholog of swip-10. In the experiments described below, using cyanogen bromide immobilized Cef for affinity capture experiments and Backscattering Interferometry (BSI) to monitor MBLAC1 binding of unmodified Cef, evidence was obtained for specific, high affinity ($K_D$=2.2 μM) binding of Cef to MBLAC1. Moreover, it was found that specific immunodepletion of MBLAC1 from brain cytosolic extracts eliminated Cef binding activity. These studies support the hypothesis that MBLAC1 is the exclusive, high-affinity binding partner of Cef in the CNS, and show the path forward in the development of novel, MBLAC1-based therapeutics for the treatment of disorders where preclinical studies demonstrate Cef effectiveness, including models of substance abuse.

To gain insight into the functional role of MBLAC1 in vivo, CRISPR/Cas9 methods were used to disrupt N-terminal coding sequences of the mouse Mblac1 gene, resulting in a complete loss of protein expression in viable, homozygous knockout (KO) animals. Using serum from both wild-type (WT) and KO mice, global, untargeted metabolomic analyses were performed, resolving small molecules via hydrophilic interaction chromatography (HILIC) based ultra-performance liquid chromatography, coupled to mass spectrometry (UPLC-MS/MS). Unsupervised principal component analysis reliably segregated the metabolomes of MBLAC1 KO and WT mice, with 92 features subsequently nominated as significantly different by ANOVA, and for which tentative and putative metabolite assignments were made. Bioinformatic analyses of these molecules nominated validated pathways subserving bile acid biosynthesis and linoleate metabolism, networks known to be responsive to metabolic and oxidative stress. These results and similar experiments performed with brain extracts can be used to identify the substrate for MBLAC1 and how substrate hydrolysis supports the anti-addiction actions of Cef. These results demonstrate the use of MBLAC1 KO animals (e.g., rodents) for demonstrating specific pathways that can be activated or suppressed by loss of MBLAC1 and demonstrate how one can use MBLAC1 KO animals (e.g., rodents) to look for specific pathways that are dependent on MBLAC1 expression (e.g., pathways through which MBLAC1-targeted therapeutic drugs reduce the actions of substances of abuse).

Described herein are methods and kits for screening candidate therapeutic agents for their ability to specifically bind a human MBLAC1 protein, to reduce the actions of a substance of abuse in a mammal, and to treat addiction to, or withdrawal from, a substance of abuse. The data presented herein provide strong support for the assertion that the well-replicated actions of Cef in the CNS arise through MBLAC1 interactions. Based on these experimental results, MBLAC1 may be used for identifying treatments for addiction to substances of abuse such as, for example, cocaine, amphetamine, morphine, ethanol, methamphetamine, clorazepate, cathinones, bath salts, heroin, nicotine, alcohol, ketamine, and MDMA.

Accordingly, described herein is a method for identifying therapeutic agents for treatment of addiction to a substance of abuse. The method includes the steps of: providing at least one test agent, MBLAC1 protein or MBLAC1-expressing cells, and Cef; and using an assay to determine whether the at least one test agent is capable of binding to MBLAC1 or disrupting binding between MBLAC1 protein and Cef. In the method, a test agent capable of MBLAC1 binding or disrupting binding between MBLAC1 protein and Cef is identified as a candidate therapeutic agent for treatment of addiction to a substance of abuse. In some embodiments, the test agent is capable of disrupting binding between MBLAC1 protein and Cef and/or binds to MBLAC1 protein with an affinity of $K_D=2$ µM or less. The substance of abuse can be any substance of abuse, including as non-limiting examples cocaine, amphetamine, morphine, ethanol, methamphetamine, clorazepate, cathinones, bath salts, heroin, nicotine, alcohol, ketamine, and MDMA. In some embodiments the MBLAC1 protein is human MBLAC1 protein. The at least one test agent can be a β-lactam antibiotic. The at least one test agent can be present in a library of test agents (e.g., a library of β-lactam structures, an organic molecule library, a peptide library, etc.). The method can further include administering the candidate therapeutic agent and the substance of abuse to at least one MBLAC1 KO animal (e.g., rodent) and to at least one WT MBLAC1 animal (e.g., rodent) and subjecting the animals to at least one test after administration of the candidate therapeutic agent and the substance of abuse. The test can be one or more of, for example, a locomotor assay, a withdrawal assay, a sensitization assay, a self-administration assay, a reinstatement to drug assay, an analysis of white matter changes, and an analysis of changes in GLTI expression. In some embodiments, the assay to determine whether the at least one test agent is capable of binding to MBLAC1 or disrupting binding between MBLAC1 protein and Cef can be one or more of microcalorimetry, surface plasmon resonance, backscattering interferometry, radioligand binding assay, and any assay that can detect binding of unlabeled small molecules and proteins.

Also described herein is a method for identifying therapeutic agents for treatment of addiction to a substance of abuse. The method includes the steps of: providing at least one test small molecule and MBLAC1 protein or MBLAC1-expressing cells; and analyzing binding between the at least one test small molecule and MBLAC1 protein, wherein the at least one test small molecule is identified as a candidate therapeutic agent for treatment of addiction to a substance of abuse if it specifically binds to MBLAC1 protein. In some embodiments, the candidate therapeutic agent specifically binds to MBLAC1 protein with an affinity of $K_D=2$ µM or less. The substance of abuse can be any substance of abuse, including, as nonlimiting examples, cocaine, amphetamine, morphine, ethanol, methamphetamine, clorazepate, cathinones, bath salts, heroin, nicotine, alcohol, ketamine, and MDMA. The MBLAC1 protein can be human MBLAC1 protein. The step of analyzing binding between the at least one test small molecule and MBLAC1 protein can be performed using any suitable assay or assays, e.g., microcalorimetry, surface plasmon resonance, backscattering interferometry, radioligand binding assay, and an assay that can detect binding of unlabeled small molecules and proteins. In some embodiments, a library of small molecules (e.g., natural product library, synthetic molecule library, etc.) includes the at least one test small molecule. The method can further include administering the candidate therapeutic agent and the substance of abuse to at least one MBLAC1 KO animal (e.g., rodent) and to at least one WT MBLAC1 animal (e.g., rodent) and subjecting the animals to at least one test after administration of the candidate therapeutic agent and the substance of abuse. Any suitable test or tests can be performed, including, as nonlimiting examples, a locomotor assay, a sensitization assay, a self-administration assay, a reinstatement to drug assay, an analysis of white matter changes, and an analysis of changes in GLTI expression.

Further described herein is a kit for identifying a therapeutic agent that reduces the actions of at least one substance of abuse. The kit includes: purified MBLAC1 protein; labeled Cef, at least one buffer; and instructions for use.

Additionally described herein is a method of using cellular extracts from tissue or cultured cells taken from WT MBLAC1 and MBLAC1 KO animals for screening for novel, Cef-like molecules in vitro. The method includes the steps of: (a) obtaining cellular extracts from tissue or cultured cells taken from WT MBLAC1 animals and from MBLAC1 KO animals; (b) subjecting the cellular extracts to a binding assay that includes incubating the cellular extracts with a library of test molecules; (c) detecting specific binding interactions that occur in the cellular extracts from WT MBLAC1 animals but not in cellular extracts from the MBLAC1 KO animals; (d) quantitatively analyzing the binding interactions in the cellular extracts from WT MBLAC1 animals to identify molecules that specifically bind MBLAC1 with high affinity; and (e) determining if the molecules identified in (d) exert cellular actions similar or identical to Cef's actions on cells in at least one in vivo drug-response test. In the method, any cellular actions exerted by an identified molecule in the at least one in vivo drug-response test are not observed in an MBLAC1 KO animal. In a typical embodiments, steps (b)-(d) are performed using any method that can detect binding reactions in cell extracts. For example, these steps can be performed using BSI. In some embodiments the animals are rodents.

Yet further described herein is a method of using cells from a MBLAC1 KO animal to test for Cef-like actions of a test molecule. The method includes the steps of: providing a first set of cells isolated from at least one WT MBLAC1 animal and a second set of cells isolated from at least one MBLAC1 KO animal; adding the test molecule to the first and second sets of cells; analyzing the first and second sets of cells for at least one cellular property or preparing cellular extracts from the first and second sets of cells and analyzing the cellular extracts for expression level changes in Cef-responsive genes, proteins or cell metabolites; comparing the at least one cellular property in the first set of cells to the at least one cellular property in the second set of cells or comparing the expression level changes in the cellular extracts from the first set of cells to the expression level changes in the cellular extracts from the second set of cells; and determining if the test molecule demonstrates one or more of the cellular actions that Cef exerts on cells in the first set of cells but not in the second set of cells. The at least one cellular property can be one or more of, for example, shape, size, respiration, and growth. The method can further include identifying any test molecule that displays the cellular actions that Cef exerts on cells as a candidate therapeutic agent for reducing the actions of at least one drug of abuse. In the method, the cellular actions that Cef exerts on cells typically includes at least one of: increasing excitatory amino acid transporter 2 (EAAT2) expression; inducing the expression of the glutamate/cystine exchanger, system $x_c^-$; increasing mRNA expression of the specific system $x_c^-$ subunit, xCT; increasing GSH release from cortical and spinal astrocytes; inducing nuclear factor erythroid 2-related factor 2 (Nrf2) expression; and protecting cells against oxidative glutamate toxicity.

As used herein, "protein" and "polypeptide" are used synonymously to mean any peptide-linked chain of amino acids, regardless of length or post-translational modification, e.g., glycosylation or phosphorylation.

By the terms "MBLAC1 protein" and "MBLAC1 polypeptide" is meant an expression product of a Mblac1 gene such as the native human MBLAC1 protein (UniprotKB Protein: A4D2B0), or a protein that shares at least 65% (but preferably 75, 80, 85, 90, 95, 96, 97, 98, or 99%) amino acid sequence identity with the foregoing. SEQ ID NO: 1 is the human MBLAC1 protein sequence.

As used herein, a "nucleic acid" or a "nucleic acid molecule" means a chain of two or more nucleotides such as RNA (ribonucleic acid) and DNA (deoxyribonucleic acid). By the term "gene" is meant a nucleic acid molecule that codes for a particular protein, or in certain cases, a functional or structural RNA molecule.

By the terms "Mblac1 gene," "Mblac1 polynucleotide," and "Mblac1 nucleic acid" is meant a native human MBLAC1-encoding nucleic acid sequence, e.g., the native human Mblac1 gene (RefSeq Accession: NC_000007.14), a nucleic acid having sequences from which a Mblac1 cDNA can be transcribed; and/or allelic variants and homologs of the foregoing. The terms encompass double-stranded DNA, single-stranded DNA, and RNA. SEQ ID NO: 2 is the human Mblac1 cDNA sequence. Within SEQ ID NO:2, base pairs 703-1503 are the coding sequence.

When referring to a nucleic acid molecule or polypeptide, the term "native" refers to a naturally-occurring (e.g., a WT) nucleic acid or polypeptide.

The terms "specifically binds to," and "specific binding" refer to that binding which is characterized by either 1) having one member of a pair interact with the other species, but not other species at a comparable affinity (selectivity) and 2) having the detectable binding signal to the species eliminated when the species is absent, mutated to be non-functional or not expressed, or chemically-denatured, or when the species is bound with another molecule or compound already known to bind specifically to this species (competition).

The terms "percent identity" and "percent identical," as known in the art, mean a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using any suitable computer program.

The term "isolated" designates a biological material (small molecule, nucleic acid or protein) that has been removed from its original environment (the environment in which it is naturally present). For example, a protein present in its natural state in a plant or an animal is not isolated, however the same protein separated from the adjacent proteins in which it is naturally present, is considered "isolated". The term "purified" means separated from many other entities (small molecules, proteins, nucleic acids, compounds), and does not require the material to be present in a form exhibiting absolute purity, exclusive of the presence of other entities. In some embodiments, a small molecule, compound, protein, nucleic acid or other entity is considered pure (purified) when it is removed from substantially all other entities.

By the terms "to modulate" and "modulates" is meant to increase or decrease. These terms can refer to increasing or decreasing an activity, level or function of a molecule (e.g., protein, peptide, nucleic acid, small molecule, metabolite), or effecting a change with respect to one or more biological or physiological mechanisms, effects, responses, functions, pathways or activities in which, for example, MBLAC1 and/or Cef are involved, such as a Cef-dependent signaling pathway or metabolic pathway.

When a molecule is referred to herein as "Cef-responsive", that term means any molecule (nucleic acid (e.g., gene), poplypeptide, peptide, small molecule or metabolite) whose level or activity is modulated (i.e., increased or decreased) by Cef.

By the term "Cef-like" is meant any molecule with a four membered, beta-lactam ring or a substituted beta lactam ring.

As used herein, "substance abuse" means the excessive use of a substance, especially alcohol or a drug, by an individual, e.g., excessive use of the drug or substance despite an understanding of the negative consequences in continued use (e.g. loss of job, loss of relationships, loss of health, loss of consciousness, loss of life).

As used herein, the terms "substance of abuse" and "drug of abuse" are used interchangeably and mean any substance or drug that is abused by an individual. Examples of substances of abuse include cocaine, amphetamine, morphine, ethanol, methamphetamine, clorazepate, cathinones, bath salts, heroin, nicotine, alcohol, ketamine, and MDMA.

The terms "agent" and "therapeutic agent" as used herein refer to a chemical entity or biological product, or combination of chemical entities or biological products, administered to a subject (a mammal such as a human) to treat a disease or condition (e.g., addiction). Examples of therapeutic agents include small molecules and biologics, which may be referred to herein as a "drug" or "therapeutic drug".

The terms "patient," "subject" and "individual" are used interchangeably herein, and mean a subject, typically a mammal, to be treated, diagnosed, and/or to obtain a biological sample from. Subjects include, but are not limited to, humans, non-human primates, horses, cows, sheep, pigs, rats, mice, dogs, and cats. A human in need of substance abuse or addiction treatment is an example of a subject.

The terms "sample," "patient sample," "biological sample," and the like, encompass a variety of sample types obtained from a patient, individual, or subject and can be used in a therapeutic drug screening, diagnostic or monitoring assay. The patient sample may be obtained from a healthy subject, a diseased patient or a patient having associated symptoms of a particular disease or disorder (e.g., addiction to a substance(s) of abuse). Moreover, a sample obtained from a patient can be divided and only a portion may be used for therapeutic drug screening. Further, the sample, or a portion thereof, can be stored under conditions to maintain sample for later analysis. The definition specifically encompasses blood and other liquid samples of biological origin (including, but not limited to, cerebrospinal fluid, plasma, serum, peripheral blood, urine, saliva, stool and synovial fluid), solid tissue samples such as a biopsy specimen or tissue cultures or cells derived therefrom and the progeny thereof. In a specific embodiment, a sample includes a cerebrospinal fluid sample. In another embodiment, a serum sample is used. The definition also includes samples that have been manipulated in any way after their procurement, such as by centrifugation, filtration, precipitation, dialysis, chromatography, treatment with reagents, washing, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

As used herein, the terms "therapeutic treatment" and "therapy" are defined as the application or administration of a therapeutic agent or therapeutic agents to a patient who has a disease, a symptom of disease or a predisposition toward a disease, with the purpose to cure, heal, alleviate, relieve, alter, remedy, ameliorate, improve or affect the disease, the symptoms of disease, or the predisposition toward disease.

Although methods and kits similar or equivalent to those described herein can be used in the practice or testing of the present invention, suitable methods and kits are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIGS. 1A-1D show detection and expression of MBLAC1. 1A: Alignment of putative MBLAC1 orthologs across phylogeny. Except for nematodes, the MBD is the primary component of these proteins. Bars represent critical residues for metal binding and catalytic activity ("x" indicates any other amino acid). MBD positioning within each protein (aa=amino acids) was established with the SMART database online tool (acquisition number SM00849). 1B: Detection of mouse and human MBLAC1 from stably-transfected T-REx cells. Cells were induced (or not) with TET prior to generation, SDS-PAGE and Western blotting of cell lysates. Antibody #79 detects human and mouse MBLAC1 (top immunoblot IB), whereas antibody #80 can only detect the mouse isoform. β-Actin blots below verify that though loaded with equivalent protein, the non-TET cells do not express MBLAC1. 1C: Subcellular fractionation of NIH 3T3 mouse fibroblast cell lysates reveal MBLAC1 expression is relegated to the cytosolic fractions, based on co-fractionation with GAPDH. 1D: Presence of MBLAC1 protein in various regions of the mouse brain. Bar graph shows normalized densitometries of bands over multiple experiments (n=6, one-way ANOVA shows no significant main effect of brain region (P>0.05).

FIGS. 2A and 2B show MBLAC1 binding to Cef-conjugated Sepharose beads. 2A: Schematic depicting Cef conjugation to CN—Br Sepharose beads via coupling to free amine group. 2B: Evidence of MBLAC1 binding to bead-conjugated Cef. Left panel shows immunoblot detection of total MBLAC1 input of T-REx cells±TET induction. Left panel shows immunoblot detection of MBLAC1 in SDS eluate from Cef-conjugated beads±preincubation of Cef (50 μM) with MBLAC1 containing extract. 2C: Quantitation of free Cef competition for binding of MBLAC1 to immobilized Cef (n=6, one-way ANOVA, Dunnett's multiple comparison test, ****($P<0.001$)). Mean reduction in MBLAC1 binding in the presence of 50 μM free Cef is 52.4±9.3%.

FIGS. 4A-4D show CRISPR/Cas9 generation of the MBLAC1 KO mouse. 4A: Gene diagram depicts the target sequence used to direct DNA cut sites in the Mblac1 genomic sequence. The protospacer adjacent motif (PAM) and protospacer sequences are highlighted and 5 bp deletion and 14 bp deletion of the KO are underlined. The top nucleic acid sequence is SEQ ID NO: 10 and the bottom nucleic acid sequence is SEQ ID NO: 11. 4B: Beginning of the protein sequences for WT and the 5 bp MBLAC1 KO, highlighting the frameshift/missense amino acid sequence and early truncation of the 5 bp MBLAC1 KO line generated and used in the present study. The top protein sequence is SEQ ID NO: 12 and the bottom protein sequence is SEQ ID NO: 13. 4C: MBLAC1 immunoblot of protein lysates prepared from WT and KO brain (cortical tissue) and liver tissue. MBLAC1 KO mouse tissue lacks the specific 27 kDa MBLAC1 band.

DETAILED DESCRIPTION

Figure 3A:
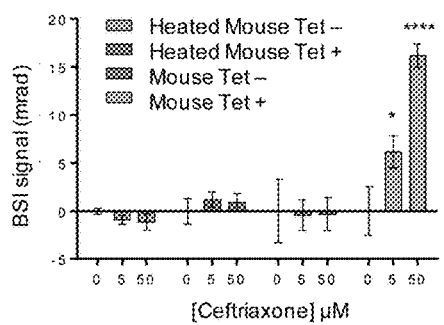
FIGS. 3A-3F show results of a BSI analysis of MBLAC1 binding to unconjugated Cef. 3A: Lysates from TET induced T-REx cells expressing mouse MBLAC1 demonstrate concentration-dependent, heat-sensitive BSI binding signals that are absent from lysates prepared from cells lacking TET induction. (TET– vs TET+ at 5 μM and 50 μM, *($P<0.05$) and **($P<0.0001$), respectively) 3B: Lysates from TET induced T-REx cells expressing human MBLAC1 demonstrate concentration-dependent, heat-sensitive BSI binding signals that are absent from lysates prepared from cells lacking TET induction. (TET– vs TET+ at 5 μM and 50 μM, *($P<0.001$) and **($P<0.0001$), respectively). 3C: Estimation of binding stoichiometry and Cef binding affinity to lysate from mouse MBLAC1 expressing cells using BSI. Single site binding equation fit to BSI binding data ($r^2=0.96$) yields a $K_D$ for binding of 2.2 μM±0.56. 3D: In contrast to Cef binding, multiple concentrations of CephC result in a non-significant reduction in BSI signal using lysates of mouse MBLAC1 expressing cells (TET– vs TET+ at 50 μM Cef($P<0.0001$), TET– vs TET+ at 5 μM or 50 μM CephC, $P>0.05$). 3E: Immunoblot of mouse frontal cortex extracts subjected to immunodepletion with MBLAC1 Ab #80 compared to IgG control immunodepleted extracts. 3F: Lysate of mouse frontal cortex shows binding signal with Cef that was abolished when MBLAC1 was immunodepleted using MBLAC1 antibody #80, or when the samples were heat inactivated prior to BSI analysis (Lysate vs depleted lysate at 5 μM and 50 μM, ($P<0.01$) and **** ($P<0.0001$), respectively). All experiments were analyzed using a two-way ANOVA and Tukey multiple comparisons tests.

The β-lactam compound Cef, and several other structural analogs, have been shown to reduce the ability of substances of abuse (e.g., cocaine, amphetamine, morphine, ethanol, methamphetamine, clorazepate, cathinones, bath salts, heroin, nicotine, alcohol, ketamine, and MDMA) to impact behavior, either upon initial administration, upon chronic administration, or following withdrawal. This action arises through complex mechanisms that appear to be unrelated to the agent's actions as an antibiotic. Rather, studies indicate an indirect ability of Cef to modulate extracellular glutamate (Glu) levels via induction of one or more cell surface Glu transporters, effects that are ultimately believed to influence signaling by dopamine (DA) in brain reward centers. Described herein is the discovery that Cef binds to the protein MBLAC1. Previously it was shown that mutation of the putative *C. elegans* ortholog of MBLAC1, SWIP-10, leads in worms to changes in Glu-dependent activation of DA neurons. To investigate the effects of loss of MBLAC1 in mammals and the requirement for MBLAC1 in the actions of drugs of abuse, MBLAC1 KO mice were developed, and in these MBLAC1 KO, a stronger locomotor response to cocaine compared to WT littermates was observed (FIG. 7), as well as a stronger response after withdrawal and readministration (sensitization) revealing a likely impact on psychostimulant-induced brain plasticities. Additionally, cocaine (10 mg/kg) injections into WT mice pretreated for 10 days with saline showed pronounced locomotor activation, with equivalent effects seen with cocaine injections give to MBLAC1 KO mice pretreated with saline. When cocaine injections to WT animals were preceded by a 10 day Cef treatment (200 mg/kg; once a day, i.p.), the locomotor activating effects of cocaine were lost. In contrast, Cef displayed no ability to attenuate cocaine actions in the MBLAC1 KO mice. Together, these findings indicate that loss of MBLAC1 expression impacts brain mechanisms constraining actions of cocaine and that MBLAC1 expression is required for the ability of Cef to exert its inhibitory actions on cocaine psychomotor activation. These data are the first evidence that MBLAC1-dependent pathways participate in, and can be pharmacologically targeted to modulate the actions of drugs of abuse. These data, described in more detail in the Examples below, support the utility of screening MBLAC1 binding partners as candidate therapeutic agents for treating addiction to substances of abuse.

Methods of Identifying Therapeutic Agents for Treatment of Addiction

Methods of identifying therapeutic agents that reduce the actions of a substance(s) of abuse in a mammal for treating addition to the substance(s) of abuse are described herein. These methods are performed in a number of ways, but typically are assays for identifying a test agent that is capable of binding to MBLAC1. Any suitable assay for analyzing and measuring binding of a test agent(s) to MBLAC1 can be used, and herein, will be generally referred to as "binding assays" and "cell-based assays". In one embodiment of a method for identifying therapeutic agents for treatment of addiction to a substance of abuse, the method includes the steps of: providing at least one test agent, MBLAC1 protein or MBLAC1-expressing cells, and optionally Cef; and using an assay to determine whether the at least one test agent is capable of specific binding to MBLAC1 or disrupting binding between MBLAC1 protein and Cef. In the method, a test agent capable of specific MBLAC1 binding or disrupting binding between MBLAC1 protein and Cef is identified as a candidate therapeutic agent for treatment of addiction to a substance of abuse. This embodiment can be carried out using binding assays or cell-based assays, or a combination thereof. These assays are described in more detail below.

Examples of drugs or substances of abuse include cocaine, amphetamine, morphine, ethanol, methamphetamine, clorazepate, cathinones, bath salts, heroin, nicotine, alcohol, ketamine, and MDMA. In addition to these specific examples, a drug or substance of abuse is any drug or substance abused by an individual and in some cases, shown to be sensitive to Cef administration in rodents.

In some embodiments of a method of identifying therapeutic agents for treatment of addiction to a substance of abuse, the MBLAC1 protein is human MBLAC1 protein and the at least one test agent is a β-lactam antibiotic. Full-length MBLAC1 protein or a fragment thereof that retains binding activity can be used. The MBLAC1 protein can be produced by any suitable method. For example, full-length MBLAC1 protein or a portion or fragment thereof can be expressed and purified from transformed bacteria, infected insect cells, transfected mammalian cells and in vitro translation of purified MBLAC1 mRNA by well-known conventional methods.

Any appropriate test agent or plurality of test agents can be tested in methods of identifying therapeutic agents for treatment of addiction to a substance of abuse. As mentioned, a test agent may be a molecule having a β-lactam structure. A test agent may be any molecule (e.g., small molecule), compound, protein, peptide, or nucleic acid. The test agent may be known prior to performing the binding assay or cell-based assay, or it may be identified after the binding assay or cell-based assay is performed. In some embodiments of the methods described herein, a test agent capable of binding MBLAC1 and/or disrupting binding between MBLAC1 protein and Cef binds to MBLAC1 protein with an affinity of a $K_D$ of 50 μM or less, e.g., 45 μM or less, 40 μM or less, 30 μM or less, 20 μM or less, 10 μM or less, 5 μM or less, 2 μM or less, etc. In some embodiments, the test agent capable of disrupting binding between MBLAC1 protein and Cef binds to MBLAC1 protein with an affinity of $K_D=2$ μM or less. Binding affinity can be measured, for example, by use of a single site binding equation fit to BSI binding data ($r^2$=0.96). In some embodiments, affinity is determined in assays where 1) the amount of specific binding of compound at equilibrium to MBLAC1 is determined as a function of compound concentration or 2) the potency of the compound to inhibit Cef binding at a fixed concentration is determined as a function of the concentration of inhibitor in a competition assay. Specific binding can be evaluated by other criteria, such as where direct binding is lost when MBLAC1 is heat or chemically denatured, when immunodepleted or when mutated to eliminate Cef binding.

In these methods, a library of test agents may be used (in a binding assay or cell-based assay). For example, a library of β-lactam structures may be used. In another example, an organic molecule library may be used. In yet another example, a peptide library may be used. Such libraries are commercially available.

Binding Assays

Any suitable binding assay can be used to identify agents (compounds, small molecules, proteins) that bind specifically to MBLAC1 (and that may be used as therapeutic agents for treatment of addiction to a substance of abuse). There are two general types of binding assays—a direct (unlabeled ligand) binding assay (e.g., BSI) and a competitive or competition (e.g., radiolabeled Cef, unlabeled ligand) binding assay. In the first type, one measures the binding of molecule X to a target as a function of X concentration (e.g., using a test molecule or library to bind to MBLAC1 using methods that do not require a labeled ligand). Specific binding should be saturable and the concentration achieving half maximal binding at equilibrium is interpreted as the affinity of X. In the Examples below, such an assay was used involving Cef and BSI to analyse binding of Cef to MBLAC1. In that assay, Cef was not labelled and its binding to MBLAC1 was detected using BSI. This is proof of concept that one can screen for molecules or compounds (agents) that bind MBLAC1 in a similar manner using BSI or another technique that does not require labelled ligands. Thus, in one embodiment of a direct binding assay, BSI is used to identify agents (compounds, small molecules, proteins) that bind specifically to MBLAC1. BSI is a free-solution, label-free molecular interaction assay technology that is based upon a highly sensitive micro-scale interferometer containing a microfluidic chip which receives samples for analysis. BSI molecular binding measurements are performed on mixtures of target and ligand (or drug target and lead compound) that have been incubated to achieve equilibrium. Both target and ligand have their own specific refractive index signature, which is measured as the mean polarizability of the sample as probed in the microfluidic channel. When ligand and target bind, they create a new and unique species, which translates as a discernable change in measured refractive index. Upon binding, many targets undergo conformational change, which serves as the primary origin of the BSI signal. Following incubation, samples are read in the BSI instrument, and binding maximum and associated equilibrium dissociation constant are derived. BSI technology and methodology is described in Bornhop et al., Science 317, 1732-1736, 2007, which is incorporated herein by reference in its entirety.

In general, the principle of the direct bindings assays used to identify agents that bind to MBLAC1 involves preparing a reaction mixture of MBLAC1 and the test agent(s) under conditions and for a time sufficient to allow the two components to interact and bind, thus forming a complex which can be removed and/or detected in the reaction mixture. The screening assays can be conducted in a variety of ways. For example, one method to conduct such an assay would involve anchoring MBLAC1 or the test agent(s) onto a solid phase and detecting MBLAC1/test agent complexes anchored on the solid phase at the end of the reaction. In one embodiment of such a method, MBLAC1 may be anchored onto a solid surface, and the test agent(s), which is not anchored, may be labeled, either directly or indirectly. In some assays, microtiter plates may conveniently be utilized as the solid phase. The anchored component can be immobilized by non-covalent or covalent attachments. Non-covalent attachment can be accomplished by simply coating the solid surface with a solution of the MBLAC1 protein and drying. Alternatively, an immobilized antibody, preferably a monoclonal antibody, specific for the MBLAC1 protein to be immobilized can be used to anchor the MBLAC1 protein to the solid surface. The surfaces can be prepared in advance and stored. In order to conduct the assay, the nonimmobilized component is added to the coated surface containing the anchored component (MBLAC1). After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; for example, using a labeled antibody specific for the previously nonimmobilized component (the antibody, in turn, can be directly labeled or indirectly labeled with a labeled anti-Ig antibody). In solid phase binding assays in which components are physically immobilized to a solid support, examples of solid supports include, but are not limited to, a microliter plate, a membrane (e.g., nitrocellulose), a bead, a dipstick, a thin-layer chromatographic plate, or other solid medium.

Alternatively, a reaction can be conducted in a liquid phase, the reaction products separated from unreacted components, and complexes detected; for example, using an immobilized antibody specific for MBLAC1 protein or the test agent to anchor any complexes formed in solution, and a labeled antibody specific for the other component of the possible complex to detect anchored complexes.

In some binding assays, MBLAC1 is joined (e.g., conjugated) to a label, where the label can directly or indirectly provide a detectable signal. Various labels include radioisotopes, fluorescers, chemiluminescers, specific binding molecules, particles, e.g. magnetic particles, and the like.

In one embodiment of a method for identifying therapeutic agents for treatment of addiction to a substance of abuse involving a direct binding assay, the method includes the steps of: providing at least one test agent, and MBLAC1 protein or MBLAC1-expressing cells; and using an assay to determine whether the at least one test agent is capable of specific binding to MBLAC1, wherein a test agent capable of specific MBLAC1 binding is identified as a candidate therapeutic agent for treatment of addiction to a substance of abuse.

In the second type of binding assay, the competition binding assay, a probe molecule that can bind the target (e.g., Cef) is mixed with a test molecule (or library of molecules) and the target (e.g., MBLAC1), and the test molecule's ability to interfere with binding between the probe molecule (e.g., Cef) and the target (e.g., MBLAC1) is analyzed. One example of this type of assay is one that tests for molecules or compounds that interfere with the binding of Cef to MBLAC1. If one can discriminate the probe from the test molecule(s), for example because the probe is fluorescently or radioactively labeled, then the signal of the probe in binding to the target will be reduced proportionately to the test compounds binding to the target, or competition with the probe. In the Examples below, this type of assay was used to monitor the loss of Cef binding as an indirect measure of the test molecule's interaction with MBLAC1; this was done with the bead pulldown assay described in the Examples below where unlabelled Cef competed for the binding of bead-bound Cef (labeled) to MBLAC1. Alternatively, for example, radioactive or fluorescent Cef can be used to test competition of unlabelled test agent for the binding of labeled Cef to MBLAC1. Typically in a competition assay, the probe and test compound are discriminated on the basis of physical properties or labels added to one and not the other such that the loss of probe binding is detected when the test compound is present. Most if not all assays that can demonstrate direct binding of one molecule to another can be adapted to show competition by a test agent (the competitive binding assay). Given the evidence herein that Cef binds to MBLAC1 when expressed in transfected cells or brain extracts (see Example 1), agents that bind to MBLAC1 can be identified via their competition for Cef binding. For example, in one embodiment, a method of identifying therapeutic agents for treatment of addiction to a substance of abuse includes measuring competition of a test agent(s) for radiolabeled Cef binding to immobilized or free MBLAC1.

In competition binding assays, MBLAC1 or Cef can be joined to a label, where the label can directly or indirectly provide a detectable indication that the two molecules are physically interacting (e.g., a detectable signal). Various labels include radioisotopes, fluorescers, chemiluminescers, specific binding molecules, particles, e.g. magnetic particles, and the like. In the presence of an unlabeled compound that binds to MBLAC1 in a mutually exclusive manner with Cef, the signal from the label will be reduced as the concentration of the competitor is increased. From concentration plots of these experiments, an apparent affinity of the unlabeled compound can be determined, and molecules with highest apparent affinity can be selected as candidate MBLAC1 ligands (and as possible candidate therapeutic agents).

In one embodiment of a method for identifying therapeutic agents for treatment of addiction to a substance of abuse involving a competition binding assay, the method includes the steps of: providing at least one test agent, MBLAC1 protein or MBLAC1-expressing cells, and Cef; and using an assay to determine whether the at least one test agent is capable of disrupting binding between MBLAC1 protein and Cef, wherein a test agent capable of disrupting binding between MBLAC1 protein and Cef is identified as a candidate therapeutic agent for treatment of addiction to a substance of abuse.

Direct and competitive binding assays are well known in the art, and a nonlimiting list of examples includes radioligand binding assays (e.g., in which Cef is radiolabeled and its binding to MBLAC1 is quantified), microcalorimetry, surface plasmon resonance, affinity-capture, BSI, chemiluminescent assay, enzyme-linked immunosorbent assay (ELISA), radioimmunoassay (RIA), fluorescence resonance energy transfer (FRET), fluorescence-activated cell sorting (FACS), bioluminescent assay, immunofluorescence assays, pull-down assays, any assay that can detect binding of unlabeled small molecules and proteins, etc.

Cell-Based Assays

The binding assays involving purified MBLAC1 described above are not the only assays that can be used in the methods of the invention (e.g., to identify any agents that specifically bind MBLAC1 protein). Additionally, cell-based assays can be used. By "cell-based assay" is meant any assay in which cells that express or contain MBLAC1 are probed with test molecules and a reaction or consequence of a reaction inside the cell or the shape or viability of the cell is quantified. To this end, cell lines (e.g., HEK-293, CHO, 3T3, HeLa, COS-7, etc.) that naturally express MBLAC1 protein or cell lines that have been genetically engineered to express MBLAC1 protein (e.g., by transfection or transduction of DNA such as a nucleic acid encoding MBLAC1) can be used. In some embodiments, a cell line that does not naturally express MBLAC1 (e.g., HEK-293) is particularly useful because one portion of the cells can be transfected to express MBLAC1 (or mutant MBLAC1) and compared to a second portion of the cells that are not transfected to express MBLAC1 (e.g., a negative control) to determine if the cellular response to a test molecule is specifically related to MBLAC1. Additionally, cells (e.g., mouse embryonic fibroblasts) from MBLAC1 KO animals (e.g., rodents) can be cultured and either the cultured cells or lysates thereof can be used to screen for candidate therapeutic agents. Examples of cultured cells include an inducible cell line expressing MBLAC1, and primary cultures from WT MBLAC1 and MBLAC1 KO animals (e.g., rodents). In some embodiments, lysates from cells transfected with MBLAC1 are used as the target for Cef rather than purified MBLAC1 protein. In some embodiments of a cell-based assay, if by binding to MBLAC1, a candidate therapeutic drug changes the growth rate of cells, or cell metabolism or cell biochemistry, and does not do so in cells from MBLAC1 KO animals (cells lacking MBLAC1), one would have a screen for an agent (candidate therapeutic agent) that is MBLAC1-specific. In such an embodiment, cells from WT MBLAC1 and MBLAC1 KO animals (e.g., rodents) can be compared, or, in an embodiment not involving animals (e.g., rodents), MBLAC1 can be disabled in cells in vitro using, for example, CRISPR/Cas9, Zinc finger nuclease or shRNA/siRNA approaches. As shown in Example 1 below, one can use lysates from cells expressing MBLAC1 or cells not expressing MBLAC1 to test for the binding of Cef to MBLAC1. Because Cef has been shown to have actions on cells that are nonmicrobial in nature and are linked to CNS actions of Cef, cultured cells from WT MBLAC1 and MBLAC1 KO animals (e.g., rodents), or cultured cells like those used in the experiments described in Example 1, can be used to screen for candidate therapeutic drugs that have one or more of the in vitro actions that Cef exerts on cell proteins, nucleic acids and metabolites. Several in vitro actions of Cef on cell proteins and metabolites have been identified, and include increasing excitatory amino acid transporter 2 (EAAT2) expression; inducing the expression of the glutamate/cystine exchanger, system $x_c^-$; increasing mRNA expression of the specific system $x_c^-$ subunit, xCT; increasing GSH release from cortical and spinal astrocytes; inducing nuclear factor erythroid 2-related factor 2 (Nrf2) expression; protecting cells against oxidative glutamate toxicity; etc. These actions are described in, for example, Lewerenz et al., J Neurochem. 2009 October; 111(2):332-43, incorporated by reference herein in its entirety.

Screening for Small Molecules that Bind MBLAC1

In some embodiments, a method of identifying therapeutic agents for treatment of addiction to a substance of abuse includes providing at least one (e.g., a plurality) test small molecule (e.g., 1, 2, 3, 4, 5, 10, 15, 20, 100, 1000, 10,000 etc.) and MBLAC1 protein or MBLAC1-expressing cells; and analyzing binding between the at least one test small molecule and MBLAC1 protein. The at least one test small molecule is identified as a candidate therapeutic agent for treatment of addiction to a substance of abuse if it specifically binds to MBLAC1 protein. Such a method can include high-throughput screening assays to identify small molecules that bind to MBLAC1. In such an embodiment, a method of identifying therapeutic agents for treatment of addiction to a substance of abuse can include an array-based assay for screening a library for small molecules that specifically bind MBLAC1. In one approach, one can make use of Cef to enable rapid and high throughput screens of small molecule chemical libraries, synthetic libraries, or natural product libraries. As one non-limiting example, in a competitive binding assay, Cef can be labeled with a convenient reporter (e.g. radiolabel, fluorescent tag, FRET tag, etc). The labeled Cef can then be allowed to bind to MBLAC1 protein. The Cef-MBLAC1 complex can then be allowed to interact with at least one test small molecule from a small molecule library, synthetic library or a natural product library and the ability of the at least one test small molecule to displace Cef from MBLAC1 or compete with Cef for binding to MBLAC1 protein can be measured. In such a manner one is able to identify small molecules that bind specifically to MBLAC1 protein and that are thus candidates for treatments for reducing the actions of a substance of abuse and thus treatments for treating or alleviating addiction. Small molecule, synthetic molecule, and natural product libraries are well known and commercially available. In some embodiments, the library screened may be a library comprised of molecules (test agents) that have structural similarities with Cef. Positive hits from a library screen can be confirmed by, for example, use of a different binding assay (any binding assay as described herein), by retesting the positive hit(s) (molecule) with heat or chemically denatured MBLAC1 protein, with a mutant MBLAC1 protein that cannot bind to Cef, or by immunodepleting MBLAC1 protein prior to a repeat binding assay.

Screening Identified Candidate Therapeutic Agents for Efficacy

In vitro and in vivo assays for screening candidate therapeutic agents that have been identified using the assays described above for addiction treatment efficacy will be apparent to one skilled in the art. The ability of a candidate therapeutic agent to treat addiction to a substance of abuse can be compared in vivo, e.g., by testing in parallel a WT MBLAC1 animal such as a rodent (e.g., a WT C57BL6/J or other rodent strain known to express MBLAC1 protein) and an MBLAC1 KO animal (e.g., rodent) made from the same strain as the WT MBLAC1 animal (e.g., rodent). Generally, the candidate therapeutic agent and the substance of abuse are administered to a WT MBLAC1 animal (e.g., rodent) and in parallel, the substance of abuse and candidate therapeutic are administered to a MBLAC1 KO animal (e.g., rodent). The animal's (e.g., rodent's) response to the substance of abuse is evaluated in the WT MBLAC1 animal and then compared to the MBLAC1 KO animal's (e.g., rodent's) response to the substance of abuse. The candidate therapeutic agent is given either once or multiple times prior to testing the sensitivity of each animal (e.g., rodent) to the substance of abuse (which could also be given once or multiple times, where physiological or behavioral actions of the substance of abuse are monitored). These actions can include changes in body temperature, blood pressure, respiration, locomotor activation, pain, seizures, willingness to act to obtain the drug (lever pressing, nosepoke, moving to area where drug is available), and physical signs of drug withdrawal. If the candidate therapeutic agent reduces or eliminates the action of the substance of abuse in the WT MBLAC1 animal but not in the MBLAC1 KO animal, the candidate therapeutic agent can be assumed to require the presence of MBLAC1 for demonstration of its anti-abuse/addiction properties.

In these methods, animals (e.g., rodents) (both KO and WT animals) can be subjected to at least one (e.g., one, two, three, four, five, etc.) appropriate drug-response (substance of abuse-response) test. Such drug-response tests are well known in the art, and are described in, for example, Abulseoud et al., Neuropsychopharmacology 39(7):1674-1684, 2014; Bell et al., Neuropharmacology 122:201-243, 2017; Philogene-Khalid et al., Behav Pharmacol. 28(6):485-488, 2017; Tallarida et al. Neurosci Lett. 556:155-159, 2013; Alajaii et al., Psychopharmacology (Berl). 228(3):419-426, 2013; Kovalevich et al., Am J Pathol. 181(6):1921-1927, 2012; I. Sondheimer & L. A. Knackstedt Behav. Brain Res. 225(1):252-258, 2011; Knackstedt et al., Biol Psychiatry 67(1):81-84, 2010; Rawls et al., Eur J Pharmacol. 584(2-3): 278-284, 2008; Sari et al., J Neurosci. 29(29):9239-9243, 2009; and J. D. Steketee & P. W. Kalivas Pharmacol Rev. 2011 63(2):348-365. These references are all incorporated herein by reference in their entireties. Examples of appropriate drug-response tests include: a locomotor assay, a withdrawal assay, a sensitization assay, a self-administration assay, a reinstatement to drug assay, an analysis of white matter changes, and an analysis of changes in GLTI expression after administration of the candidate therapeutic agent and the substance of abuse.

Generally, in these methods of testing candidate therapeutic drugs in combination with substances of abuse in WT MBLAC1 and KO MBLAC1 animals (e.g., rodents), Cef is active in WT MBLAC1 animals (i.e., animals in which MBLAC1 is expressed and functional) in reducing the actions of drugs of abuse, as shown in the experiments described below involving cocaine and locomotion. In the MBLAC1 KO animals, Cef action is lost. So one can test candidate therapeutic drugs that come through a primary screen (e.g., one or more of the binding assays or the cell-based assays described herein) for ones that require MBLAC1 to act to reduce the actions of drugs of abuse.

MBLAC1 Knock-Out Animals

In the experiments described herein, MBLAC1 KO rodents were used. However, any MBLAC1 KO animal whose Mblac1 orthologous gene is disrupted (mutated, eliminated, truncated) can be used, e.g. fish, insects (e.g., flies), worms, etc. Cef has been found to have actions on planarians (flatworms) to actions of drugs of abuse, thus planarians are an example of an MBLAC1 KO animal that can be generated and used in the methods described herein. Methods of identifying an MBLAC1 orthologue in an animal of interest are well known. See, for example, Example 1 below, which describes a bioinformatics analysis that identified MBLAC1 as the mammalian orthologue of swip-10 in *C. elegans*.

MBLAC1 Knock-Out Rodents

In one embodiment of a MBLAC1 KO rodent (e.g., mouse, rat) as described herein, the MBLAC1 KO rodent has no functional copies of the Mblac1 gene (i.e., lacks both copies of the Mblac1 gene or lacks portions thereof). A MBLAC1 KO rodent as described herein includes a rodent in which the mRNA expression or mRNA translation of the Mblac1 gene has been significantly reduced by chemical or genetic means. A functional MBLAC1 KO rodent expresses full length MBLAC1 protein but has a sequence change shown to completely disable function. Herein, both types of animals are termed MBLAC1 KO. The MBLAC1 KO rodent may have had its gene modified constitutively or conditionally, e.g. at a specific stage of development or in a specific tissue or brain region. In one embodiment of an MBLAC1 KO rodent, N-terminal coding sequences of the Mblac1 gene are disrupted by CRISPR/Cas9 resulting in a complete loss of MBLAC1 protein expression in the MBLAC1 KO rodent. In one such embodiment, the Mblac1 gene includes a 5 base pair deletion that disrupts the reading frame for protein translation. A MBLAC1 KO rodent can be any type of rodent, including rats and mice. Generation and validation of the MBLAC1 KO rodent is described below in Example 2. An MBLAC1 KO rodent as described herein provides a tool to analyze the mechanisms supporting the ability of β-lactam antibiotics (e.g., Cef) to suppress cocaine actions in a mammal exposed to cocaine, and to elucidate fundamental biochemical and cellular networks that support the actions of addictive and/or therapeutic psychostimulants. Additionally, an MBLAC1 KO rodent as described herein is a useful tool for testing the ability of a candidate therapeutic agent, identified using any of the assays described herein, to treat addiction to a substance of abuse.

As described above, cells from WT MBLAC1 and MBLAC1 KO rodents can be used to test for candidate therapeutic agent specificity, in combination with the use of the WT MBLAC1 and MBLAC1 KO rodents. In one example of such an embodiment, the substance of abuse is added to the cells to evoke an in vitro response (e.g., growth, shape, metabolic rate, biochemical changes) shown to be dependent on MBLAC1 protein. Using the WT MBLAC1 and MBLAC1 KO cells tested in parallel, the user would first validate the response is present with Cef application to the WT MBLAC1 cells and absent in the MBLAC1 KO cells. Then, they could evaluate their candidate therapeutic agents on the WT MBLAC1 and MBLAC1 KO cells and look for those that show a response in the former but not the latter cells. Because cells are more high-throughput than animals, the user could consider use of this assay as a primary screen for MBLAC1-targeted therapeutic drugs and then test them for their ability to impact the actions of substances of abuse in vivo in WT MBLAC1 and MBLAC1 KO rodents. Because rodents are low throughput, they can be used as a secondary screen for in vivo activity and to relate to the in vivo actions of substances of abuse.

Kits

Described herein are kits for identifying therapeutic agents for treatment of addiction to a substance of abuse. The kits can be used to conduct or facilitate binding assays and cell-based assays as described herein. A typical kit includes purified MBLAC1 protein, labeled Cef, and instructions for use. Such a kit can be used to test a set of test molecules (e.g., a library) for their ability to reduce the binding of Cef to MBLAC1. In one example of a such a kit, the kit includes purified MBLAC1 protein and labeled Cef in appropriate buffers to insure adequate Cef/MBLAC1 binding. Such a kit can have MBLAC1 or Cef as free molecules or bound to a physical surface (beads, strips or plates) to facilitate establishment of the assay being conducted (e.g., binding assay, cell-based assay). Another example of a kit includes cells from WT MBLAC1 and MBLAC1 KO animals (e.g., rodents). Such a kit can be used for screening of test molecules that show responses like Cef does on cells from WT MBLAC1 animals (e.g., rodents) but lack that activity in the MBLAC1 KO cells. Molecules or compounds that show such responses could be selected for further testing in assays of the actions of substances of abuse in cells or animals. Another example of a kit includes cells transfected with or without genetic material encoding DNA that expresses MBLAC1 constitutively or after induction with a chemical gene inducer such as tetracycline. Kits also typically include a container and packaging. Instructional materials for preparation and use of the kit components are generally included. While the instructional materials typically include written or printed materials, they are not limited to such. Any medium capable of storing such instructions and communicating them to an end user is encompassed by the kits herein. Such media include, but are not limited to electronic storage media (e.g., magnetic discs, tapes, cartridges, chips), optical media (e.g., CD ROM), and the like. Such media may include addresses to internet sites that provide such instructional materials.

Additional Methods

Also described herein are methods of using cellular extracts from tissue or cultured cells taken from WT MBLAC1 and MBLAC1 KO animal (e.g., rodent) cells for screening for novel, Cef-like molecules in vitro. A typical method includes the steps of: obtaining cellular extracts from tissue or cultured cells taken from WT MBLAC1 animals and from MBLAC1 KO animals; subjecting the cellular extracts to a binding assay including incubating the cellular extracts with a library of test molecules; detecting specific binding interactions that occur in the cellular extracts from WT MBLAC1 animals but not in cellular extracts from the MBLAC1 KO animals; quantitatively analyzing the binding interactions to identify molecules that specifically bind MBLAC1 with high affinity (e.g., $K_D<2$ μM); and determining if the molecules identified exert cellular actions similar or identical to Cef's actions on cells in at least one in vivo drug-response test, [0056] wherein any cellular actions exerted by an identified molecule in an in vivo drug-response test are not observed in an MBLAC1 KO animal (e.g., in an analogous drug-response test involving an MBLAC1 KO animal). In the method, any suitable binding assay that can detect binding reactions in cell (cellular) extracts can be used. One example of such a binding assay is BSI. When referring to molecules that specifically bind MBLAC1 with high affinity, what is meant by "high affinity" is typically an inhibition of ≥50% activity at 50 μM. In some embodiments, high affinity indicates a $K_d$ of about 2 μM or less, and in some embodiments, a $K_d$ in the nanomolar range.

Further described herein are methods of using cells from a MBLAC1 KO animal (or any cells lacking a functional Mblac1 gene) to test for Cef-like actions of a test molecule. A typical method includes the steps of: providing a first set of cells isolated from at least one WT MBLAC1 animal and a second set of cells isolated from at least one MBLAC1 KO animal; adding the test molecule to the first and second sets of cells; analyzing the first and second sets of cells for at least one cellular property or preparing cellular extracts from the first and second sets of cells and analyzing the cellular extracts for expression level changes in Cef-responsive genes, proteins or cell metabolites; comparing the at least one cellular property in the first set of cells to the at least one cellular property in the second set of cells or comparing the expression level changes in the cellular extracts from the first set of cells to the expression level changes in the cellular extracts from the second set of cells; and determining if the test molecule demonstrates one or more of the cellular actions that Cef exerts on cells in the first set of cells but not in the second set of cells. In an alternative embodiment of the method, cells lacking a functional Mblac1 gene that are not from a MBLAC1 KO animal can be used instead of cells from a MBLAC1 KO animal. Such cells lacking a functional Mblac1 gene can either be cells that naturally lack a Mblac1 gene, or they can be cells that have been modified (engineered) such that they do not contain, express or translate efficiently a Mblac1 gene. The method can also include a Cef positive control, e.g., WT MBLAC1 and MBLAC1 KO cells to which Cef has been added. These positive control Cef-treated cells can be analyzed, and/or extracts therefrom can be analyzed. Cef has been shown to have effects on cell viability. See Lewerenz et al., Journal of Neurochemistry 2009 (11):332-343, incorporated herein by reference in its entirety, which describes Cef's effects on cell number in mice treated with Cef. Examples of cellular properties to be analyzed include: shape, size, respiration, growth, etc. As cells die, they round up, float off the plate or lyse. As cells get sick, levels of cellular respiration change. Assays that monitor these intermediate phenotypes prior to cell death can be assayed. Cellular properties can be analyzed by any suitable method(s), e.g., microscopic visualization or indirect techniques. Cef's actions (Cef-like actions) on cells include increasing EAAT2 expression; inducing the expression of the glutamate/cystine exchanger, system $x_c^-$; increasing mRNA expression of the specific system $x_c^-$ subunit, xCT; increasing GSH release from cortical and spinal astrocytes; inducing Nrf2 expression; protecting cells against oxidative glutamate toxicity; etc. The method can further include identifying any test molecule that displays Cef-like actions (i.e., one or more of Cef's actions on cells) as a candidate therapeutic agent for reducing the actions of at least one drug of abuse.

EXAMPLES

The present invention is further illustrated by the following specific examples. The examples are provided for illustration only and should not be construed as limiting the scope of the invention in any way.

Example 1—Metallo-β-Lactamase Domain-Containing Protein 1 (MBLAC1) is a Specific, High-Affinity Target for the Glutamate Transporter Inducer Ceftriaxone The hypothesis that MBLAC1 is an endogenous, CNS-expressed binding partner for Cef was tested using affinity chromatography and Backscattering Interferometry (BSI). As shown below, these complementary approaches demonstrate specific, high-affinity, temperature-sensitive binding between MBLAC1 and Cef in cell and brain lysates. Moreover, immunodepletion studies support MBLAC1 as a major, if not exclusive, CNS target for the antibiotic.

RESULTS

Using the proteinBLAST tool, multiple candidate SWIP-10 orthologs across phylogeny (FIG. 1A) were identified. All proteins share a single MBD that comprises the majority of the coding sequence, whereas SWIP-10 and nematode orthologs (see *C. briggsae* in FIG. 1A) possess a much longer N-terminus with no identified functional domains. The MBDs of each protein illustrated share His and Asp residues characteristic of metal binding and catalysis, respectively. At present, an endogenous substrate(s) for these proteins has yet to be identified.

To study the putative mouse and human orthologs of SWIP-10, MBLAC1, rabbit polyclonal antisera against MBLAC1 fusion proteins were raised and purified, and stably transfected cell lines that, in the presence of TET, express mouse or human MBLAC1 (FIG. 1B) were generated. Both antibody #79 and #80 detected mouse MBLAC1 in extracts of TET-induced HEK-cells, whereas only #79 detected human MBLAC1. Antibody #80 also detects MBLAC1 in rat brain lysates. Neither antibody detected a protein of the equivalent mass as MBLAC1 in non-induced cells.

To determine the subcellular localization of endogenous MBLAC1 protein, a subcellular fractionation protocol was implemented using extracts of mouse NIH 3T3 cells (FIG. 1C). Identity of cytosolic, organelle (e.g. ER), and nuclear fractions were confirmed by immunoblotting with antibodies targeted to compartment-specific proteins. MBLAC1 protein was found to localize to cytosolic fractions characterized by glyceraldehyde 3-phosphate dehydrogenase (GAPDH) enrichment (FIG. 1C). Owing to the CNS being the likely site of action for the behavioral actions of Cef, mouse brain extracts were blotted for the presence of MBLAC1 protein. Consistent with a relatively even pattern of MBLAC1 mRNA expression detected across mouse brain regions in a prior study (Hardaway et al., The Journal of Neuroscience vol. 35, p. 9409-9423, 2015), statistically equivalent levels of anti-MBLAC1 immunoreactive protein were detected in extracts of hippocampus, striatum, cortex, cerebellum, and midbrain (FIG. 1D). Although affinity-purified antibody #80 proved suitable for detection of MBLAC1 protein in tissue extracts (see also FIG. 3E), other bands are evident on tissue western blots suggesting that immunocytochemistry pursued with this reagent is likely of insufficient specificity for evaluation of MBLAC1 regional distribution.

To determine if MBLAC1 and Cef interact, a MBLAC1 pulldown assay using Cef-conjugated CN—Br activated Sepharose beads was developed (FIG. 2A). Conjugated and unconjugated beads were incubated with lysates from TET or non-TET induced T-REx cells (FIG. 2B). Cef-conjugated beads extracted significantly more MBLAC1 from lysates than unconjugated beads, with no evidence of MBLAC1-immunoreactive species detected when Cef-conjugated beads were incubated with uninduced cell extracts. To further assess specificity and affinity between these two molecules, MBLAC1 expressing cell lysates were incubated with Cef (50 µM) prior to incubation with Cef-conjugated beads, which significantly diminished MBLAC1 capture (FIG. 2C).

Figure 3B:
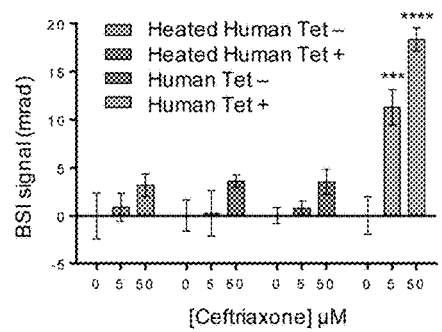

Although the pulldown approach provided initial evidence of Cef interactions with MBLAC1, the efficiency of competition was lower than expected, based on prior studies reporting the in vitro potency of Cef for GLT-1 induction. It was reasoned that steric hindrance could limit high-affinity interactions of MBLAC1 with Cef-conjugated beads. As radiolabeled Cef was unavailable, a non-isotopic approach that could examine Cef/MBLAC1 interactions without ligand immobilization was sought. Backscattering interferometry is a sensitive approach that can detect both kinetic and equilibrium associations of unlabeled, small molecule interactions with unmodified target proteins (Bornhop et al., Science vol. 317, 1732-1736, 2007). Using lysates from uninduced and induced T-REx cells expressing mouse or human MBLAC1, BSI was implemented as described below and significant, dose-dependent BSI signals were detected only in induced cell lysates (FIG. 3A, 3B). BSI signals were eliminated by heat denaturation of extracts prior to analysis, consistent with Cef binding as arising from a proteinaceous species versus TET used to induce MBLAC1 expression.

Figure 3C:
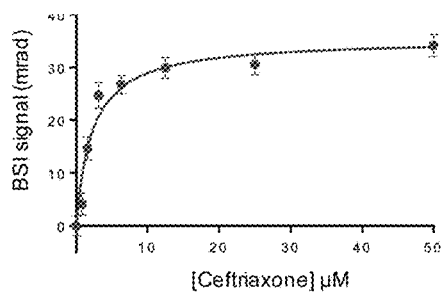

The BSI results noted above both confirmed the Cef/MBLAC1 interactions detected in Cef-conjugated bead assays and also established a quantitative approach that could be used to estimate the affinity of unconjugated Cef for MBLAC1. Indeed, binding data collected in BSI assays conducted across a range of Cef concentrations were well fit (r2=0.96) to a single site binding equation with a $K_D$ of 2.2+/−0.56 µM (FIG. 3C).

Figure 3D:
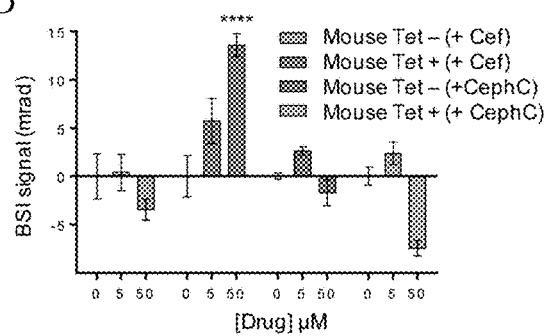

To explore the promiscuity of MBLAC1 interaction with other β-lactam antibiotics, BSI signals with cephalosporin C (CephC) were compared to those obtained with Cef. Significant dose-dependent BSI signals were again detected with Cef, but a significant CephC BSI signal (FIG. 3D) was not seen. Though these data are not statistically significant, the negative BSI signal observed in the presence of CephC indicates that there may be an interaction between MBLAC1 and CephC at high concentrations, though the nature of this interaction would appear to be molecularly different from the interaction we observe between Cef and MBLAC1. These findings further solidify the hypothesis that Cef/MBLAC1 interactions account for the reported nonmicrobial actions of Cef in the CNS.

Figure 3E:
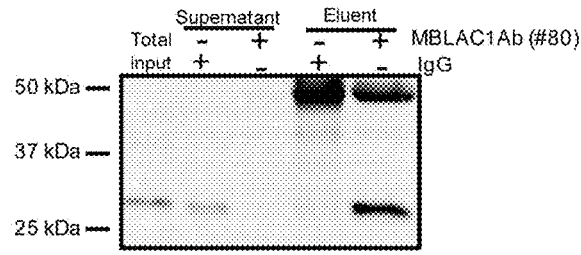
Figure 3F:
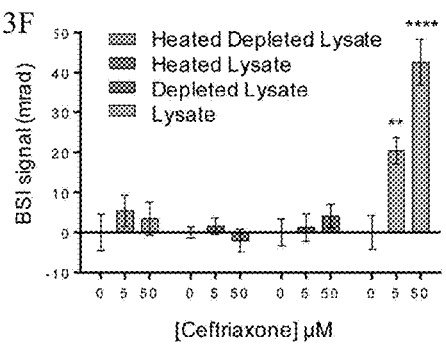

To detect endogenous Cef binding and to determine whether MBLAC1 is likely to be responsible for observed interactions, the BSI experiments were repeated using mouse frontal cortex lysates, with and without prior heat denaturation. To determine whether, and to what degree, Cef binding signals derive from MBLAC1, BSI studies were performed on lysates that had been immunodepleted of MBLAC1 protein by anti-MBLAC1 antibody (#80). Clearance of frontal cortex lysate using MBLAC1 antibody, but not control antiserum, resulted in the elimination of MBLAC1 protein from cortical extracts (FIG. 3E). When BSI binding assays were conducted with immunodepleted extracts, the Cef binding signal was abolished (FIG. 3F). These findings support the contention that, under these binding conditions, MBLAC1 is likely the primary species in brain lysates capable of interacting with Cef at high-affinity—that the well-replicated actions Cef in the CNS arise through MBLAC1 interactions.

METHODS

Materials and Animals

All biochemical reagents, salts and buffers were obtained from Sigma-Aldrich (St. Louis, Mo.) unless otherwise specified, and were of the highest quality available. All experiments with animals were performed under a protocol approved by the Vanderbilt Institutional Animal Care and Use Committee (IACUC). Studies with mice utilized animals of the C57BL/6J strain obtained from Jackson Laboratories (Bar Harbor, Me.).

Polyclonal Antibody Generation

Mouse brain mRNA was isolated as described and then Mblac1 cDNA was amplified by PCR prior to cloning in frame with glutathione S-transferase (GST) in pGEX2T (GE Healthcare Life Sciences, Chicago, Ill.), followed by transformation into BL21 cells (New England Biolabs, Ipswich, Mass.). Expression of GST-mouse MBLAC1 fusion protein was induced using 0.3 mM isopropyl β-D-1-thiogalactopyranoside (IPTG) and purified from bacterial cells via affinity chromatography using glutathione-coupled Sepharose® (GE Healthcare, Chicago, Ill.), following manufacturer's protocol. Purified GST-mouse MBLAC1 with adjuvant was injected into two rabbits (#4979 (#79) and #4980 (#80), Thermo Fisher, Waltham, Mass.) and boosted monthly to produce antiserum. To purify antisera, mouse Mblac1 cDNA was cloned in frame with maltose binding protein (MBP) coding sequences in pMa1-cRI (New England Biolabs, Ipswich, Mass.). Full length MBP-mouse MBLAC1 protein was generated as described for GST-mouse MBLAC1, with addition of 100 µM $ZnSO_4$ to the culture media during induction. MBP-mouse MBLAC1 fusion protein was purified via affinity chromatography over amylose resin (New England Biolabs, Ipswich, Mass. USA) and concentrated by spin filtration. To remove GST-directed antibodies, antisera were incubated with MBP-mouse MBLAC1-conjugated amylose, followed by multiple washes in column buffer (20 mM Tris-HCl, 200 mM NaCl, 1 mM EDTA, pH 7.4). Bound antibodies were eluted with 150 mM glycine pH 2.0, collecting 400 µL fractions into 2M Tris-HCl pH 8.0 for neutralization. Samples were pooled and dialyzed in 1×PBS (290 mM NaCl, 3 mM KCl, 10 mM $NaHPO_4$, 1.8 $KH_2PO_4$,) at 4° C. overnight. Dialysate was then concentrated by spin filtration and assayed for protein content (Bradford, Bio-Rad, Hercules, Calif.).

HEK Inducible Cell Line Generation

HEK Flp-In T-REx-293 cells (T-REx) expressing mouse or human MBLAC1 proteins were generated per manufacturer's (ThermoFisher, Waltham, Mass., USA) instructions. Briefly, mouse and human Mblac1 cDNAs were subcloned into pcDNA5/FRT/TO vector and then co-transfected with pOG44 plasmid (encoding Flp recombinase) by lipid based transfection into Flp-In T-REx-293 cells using TransIT-LT1 (Mirus, Madison, Wis.). Stable integrants were isolated following selection with 100 µg/ml hygromycin. Expression of MBLAC1 protein was induced by addition of 1 µg/mL tetracycline (TET) to the media. Maintenance media contained 15 µg/mL blasticidin (Life Technologies/ThermoFisher, Waltham, Mass.), 100 µg/mL hygromycin B (Life Technologies/ThermoFisher, Waltham, Mass.) as selection agents, in addition to 10% fetal bovine serum (Gibco/ThermoFisher, Waltham, Mass.), 2 mM L-glutamine, and 100 Units/mL penicillin-100 µg/mL streptomycin.

Western Blotting

Protein samples for Western blot analysis were quantified for total protein (BCA Pierce/ThermoFisher, Waltham, Mass.) and heated to 95° C. for 5 min with 1× Laemmli buffer before separation via SDS-PAGE using 10% polyacrylamide gels and transfer to Immobilon PVDF membranes (Millipore, Billerica, Mass.). Membranes were blocked for 1 hr at room temp (RT) with 5% milk in TBS/0.1% TWEEN (TBST). Primary antibody, diluted 1:1000 in 5% milk/TBST, was incubated with membranes overnight at 4° C. After washing 4× for 5 min with TBST, secondary antibody (peroxidase-conjugated mouse-anti-rabbit, Jackson ImmunoResearch, West Grove, Pa.) in 5% milk/TBST was incubated for 1 hr at RT. Blots were washed again before band visualization and quantitation by enhanced chemiluminescence (BioRad Clarity ECL, Hecules, Calif.) using an ImageQuant LAS 4000 imager (GE Heathcare Life Sciences, Chicago, Ill.).

Subcellular Fractionation

Plated 3T3 cells were washed in PBS and pelleted for resuspension in a digitonin buffer (150 mM NaCl, 50 mM HEPES, 200 µg/mL digitonin) for 10 min while rotating. Lysate was then spun at 2000×g and resultant supernatant was kept (cytosolic fraction). The remaining pellet was resuspended in an NP40 buffer (150 mM NaCl, 50 mM HEPES, 1% NP40) and lysate was left on ice in NP40 buffer for 30 min and then centrifuged at 7000×g. Resultant supernatant was kept for membrane and organelle fraction, whereas the pellet was resuspended in RIPA buffer (150 mM NaCl, 50 mM HEPES, 0.5% Na-deoxycholate, 0.1% SDS, 1 U/ml Benzonase) and rotated for 1 hr at 4° C. then centrifuged for 10 min at 7000×g. Supernatant was kept for nuclear protein fraction. Each fraction was then subjected to Western blot analysis as described above.

Immunodepletion Studies

Wild type C57BL/6J mice (Jackson Labs, Bar Harbor, Me.) were rapidly decapitated and frontal cortex was dissected. Tissue was homogenized in ice cold 20 mM HEPES buffer (pH 7.4) using a Dounce homogenizer (Wheaton, Millville, N.J.), and then sonicated (F60 sonic dismembrator, Fisher Scientific, Waltham, Mass.) using 5, 1 sec pulses. Lysates were then centrifuged at 100,000×g for 30 min. Supernatants were collected, diluted with 2× lysis buffer (40 mM HEPES, 220 mM KCl, 20 mM NaCl, 4 mM MgCl, 10 mM $KH_2PO_4$, 500 µM $ZnSO_4$) and protein concentration determined (BCA Protein Assay, ThermoFisher, Waltham, Mass.). Lysates were incubated at 4° C. overnight with 5 µg of either rabbit IgG (Antibodies Inc., Davis, Calif.) or affinity-purified MBLAC1 antibody #80. Samples were then incubated with Magnetic Protein G beads (Dynabeads, ThermoFisher, Waltham, Mass.) for 2 hr at 4° C. Supernatants were removed for BSI and Western blot analysis. A portion of supernatants were heat denatured at 95° C. for 5 min prior to BSI experiments (see below). Beads were washed 3× with 1× lysis buffer and MBLAC1 protein was eluted with 4× Laemmli buffer and diluted prior to SDS PAGE and Western blot analysis.

Affinity Capture of MBLAC1 with Cef-Conjugated Sepharose®

Cyanogen Bromide (CN—Br) Activated Sepharose® 4B beads were prepared and conjugated to Cef following manufacturer's recommendations (GE Healthcare Life Sciences, Pittsburgh, Pa.). Briefly, lyophilized beads were suspended and washed 3× in 1 mM HCl, pH 3.0. Beads were then equilibrated in coupling buffer (500 mM NaCl, 0.1 mM $NaCHO_3$, pH 8.3), and divided into conjugated and unconjugated samples. Conjugated beads (250 µL) were left to rotate for 1 hr at room temp with 2.5 moles of Cef in coupling buffer. The unconjugated beads were treated the same except no Cef was added. After coupling, remaining reactive CN—Br groups were inactivated by incubation (3 hr) with 0.1M Tris-HCl (pH 8.0). Following inactivation, beads were subjected to alternating acid/base washes with 0.1M Na-acetate (pH 4.0) and 0.1M Tris-HCl (pH 8.0). Beads were then equilibrated in lysate buffer prior to lysate addition. Final protein concentrations (100 µg protein at 0.1 mg/mL) were incubated for 1 hr at room temp with 50 µL beads (50% slurry). In competition experiments, excess Cef (50 µM, final concentration) was mixed with lysates 10 min prior to addition of beads at room temp. Beads were washed 5× in lysis buffer prior to elution of bound MBLAC1 in 2× Laemmli buffer, followed by SDS-PAGE and Western blot analysis.

Backscattering Interferometry Binding Assays

To assess the binding of unlabeled Cef with MBLAC1 in cell and tissue lysates, BSI was utilized. A BSI instrument was assembled and employed (Kussrow et al., Anal Chem 84, 779-792, 2012). Briefly, BSI, using a semi-circular chip, a helium-neon laser, and CCD camera, allows for high-sensitivity, refractive index (RI) sensing. The RI signal is obtained by isolating shifts in the backscattered fringes by Fourier analysis. RI changes are quantified by comparing fringe shifts between test and reference samples.

Lysates for BSI contained Cef at concentrations of 0 µM, 5 µM, and 50 µM and concentrations of either 300 µg/mL (mouse cell lysates) or 100 µg/mL (human cell lysates and mouse brain lysates) protein. Samples were incubated on ice for 1 hr prior to analysis to favor equilibrium binding conditions. To obtain BSI signals, the sample with 0 µM Cef was injected into the channel in a stop-flow manner using a vacuum and allowed to reach temperature and pressure equilibrium (~10 sec) at which point the phase value (BSI signal) was measured for 20 sec. Specific BSI signal was determined by subtracting Cef only signal from Cef-lysate signals. To determine binding affinity, BSI was conducted as above using Cef concentrations ranging from 0.78 µM to 50 µM. Signals were plotted versus concentration and fitted with a single-site saturation binding curve using Prism 6.0 software (GraphPad, Inc., La Jolla, Calif.).

Example 2—Global Untargeted Serum Metabolomic Analyses Nominate Metabolic Pathways Responsive to Loss of Expression of the Orphan Metallo β-Lactamase, MBLAC1

Above in Example 1 it was shown that MBLAC1 is a specific, and possibly exclusive, high-affinity target for the β-lactam antibiotic, Cef. Multiple studies reveal that Cef can elevate glial expression of plasma membrane Glu transporters that can normalize pathologically altered extracellular Glu levels. However, neither the endogenous substrate nor an ascribed metabolic pathway, have been established for MBLAC1, though the ability of Cef to afford neuroprotection against Glu related pathology in many brain disorders and block reinstatement to drugs of abuse after withdrawal, suggests that advances in substrate and pathway elucidation may be of clinical significance. Although there is significant functional information in worms concerning the cellular and physiological impact of swip-10 mutations, the gene is expressed in a small number of cells, making a biochemical comparison between wildtype and mutant strains problematic. In contrast, the murine Mblac1 gene is widely expressed. Thus, in these experiments, biochemical differences between wildtype (WT) and MBLAC1 knockout (KO) mice were characterized, the KO mice produced using a CRISPR/Cas9 approach. Here both the successful generation of viable MBLAC1 knockout (KO) mice and efforts to use these animals to investigate the in vivo biochemical impact of loss of MBLAC1 expression are reported. These results demonstrate the use of the KO mice for demonstrating specific pathways that can be activated or suppressed by loss of MBLAC1 and demonstrate how one can use the KO mice to look for specific pathways that are dependent on MBLAC1 expression Here the results of these efforts to interrogate the serum metabolome of MBLAC1 KO and age-matched WT mice are reported. To resolve serum small molecules responsive to loss of MBLAC1 expression, an ultra-performance liquid chromatography coupled to mass spectrometry (UPLC-MS/MS)-based analysis was implemented. Reported are the presence of unique biosignatures that distinguish the sera of MBLAC1 KO from WT mice, with replicated, over-representation of features linked to primary bile acid biosynthesis and linoleate metabolism. These networks are discussed in the context of the biology of the MBLAC1 ortholog SWIP-10, as well as the neuroprotective actions of chronic Cef administration.

METHODS AND MATERIALS

Generation of MBLAC1 KO Mice

Initial untargeted metabolomics experiments and generation of the MBLAC1 KO mice were performed under a protocol approved and annually reviewed by the Vanderbilt Institutional Animal Care and Use Committee. For a subsequent pathway validation metabolomic study, experiments were performed under a protocol approved and annually reviewed by the Florida Atlantic University Institutional Animal Care and Use Committee. In all experiments, mice were housed on a 12:12 LD cycle with food and water available ad libitum. To implement a CRISPR/Cas9 based strategy for producing MBLAC1 KO mice, software developed in the Zhang laboratory (Massachusetts Institute of Technology) was utilized to evaluate sequences in the first exon, where an optimal protospacer adjacent motif (PAM) sequence located 43-45 bp 3' of the ATG start site was identified. A guide RNA was generated with sequence that matched the protospacer adjacent to the PAM—3' to 5': GGAAACGACCGCAGGTCGCCG (SEQ ID NO:3) (PAM site underlined). Sense and antisense oligonucleotides (Sigma Aldrich, St. Louis, Mo.) encoding the guide RNA were annealed and inserted into the plasmid pX330 (Addgene plasmid #42230) which also encodes CAS9 (Cong et al., Science 2013 DOI: science.1231143 [pii]10.1126/science.1231143). Injection of the plasmid into C57BL6/J embryos was performed in the Vanderbilt ES/Transgenic Mouse Core. From these injections one male pup was identified as having a 5 bp deletion at the targeted site, deleting bp 46-50, and another male pup was identified as having a 14 bp deletion at the targeted site, deleting bp 44-57, as verified by Sanger sequencing (Genewiz). KO mice referred to in the present study represent progeny of the 5 bp deletion founder. Genotyping of MBLAC1 KO mice was performed by TransnetYX, Inc (Cordova, Tenn., USA) using separate PCR reactions to genotype for WT (forward primer: GACAGCGATAGTTTAGTTTC (SEQ ID NO: 4), and reverse primer: TTGCTGGCGTCCAGCGGC) (SEQ ID NO:5), 5 bp deletion MBLAC1 KO (forward primer: GACAGCGATAGTTTAGTTTC (SEQ ID NO: 6) and reverse primer: TCCCTGGCGTCCAGCGGC) (SEQ ID NO:7) and 14 bp deletion MBLAC1 KO (forward primer: CGAGCCCCTGCATCCT (SEQ ID NO: 8) and reverse primer: GCCGCGCAGCAGAAC) (SEQ ID NO:9). KO mice were mated with WT C57BL6/J females and heterozygous KO pups were outcrossed to C57BL6/J mice for 3 additional generations to limit the presence of off-target mutations in mice used for analysis.

Evaluation of MBLAC1 Protein Expression by Western Blotting

All chemicals used in tissue homogenization and immunoblotting assays, unless otherwise specified, were obtained from Sigma-Aldrich (St. Louis, Mo., USA). For western blots to validate loss of MBLAC1 protein, male mice were killed by rapid decapitation and whole brains were removed to an ice-cold metal plate and dissected into specific regions. Freshly dissected brain regions were homogenized in RIPA buffer (50 mM Tris, pH 7.4, 150 mM NaCl, 1 mM EDTA, 1% TRITON X-100, 1% sodium deoxycholate, 0.1% SDS) with a Dounce homogenizer and then solubilized for 1 hr at 4° C. while rotating. Protein lysates were centrifuged at 4° C. for 30 min at 15,000×g to remove insoluble material. Protein concentrations of supernatants were determined using the BCA method (ThermoFisher, Waltham, Mass., USA) and 40 µg of brain (cortical tissue) protein and 60 µg of liver protein was separated by 10% SDS-PAGE, transferred to PVDF membranes (Miillipore Sigma, Billerica, Mass., USA). Membranes were blocked using 5% dry milk in TBS/0.1% Tween (TBST) for 1 hr at room temperature (RT) prior to incubation with affinity-purified MBLAC1 #4980 antibody (1:1000 dilution in 5% milk with TBST—incubated overnight at 4° C. followed by 4×5 minutes with TBST). HRP-conjugated, mouse anti-rabbit secondary antibody (Jackson ImmunoResearch, West Grove, Pa.) was used at 1:10000 dilution. B-Actin was detected using a 1:20,000 dilution of β-actin-HRP antibody (Sigma-Aldrich, St. Louis, Mo.). Immuno-reactive bands were identified by chemiluminescence (Clarity, BioRad, Hercules, Calif., USA) and imaged with an LAS4000 imager (GE Healthcare Life Sciences, Pittsburgh, Pa., USA) and analyzed with associated ImageQuant™ software (GE Healthcare Life Sciences, Pittsburgh, Pa., USA).

Serum Sample Preparation

The initial untargeted study made use of serum collected from three, age- (12-16 wks) and sex- (female) matched WT and KO mice. WT mice were commercially obtained C57BL/6J mice (Jackson Labs, Bar Harbor Me., USA). The subsequent pathway validation study reported is derived from serum collected from four sex-(female) matched WT and KO littermates (aged 12-16 weeks) bred from MBLAC1 heterozygous parents. Following rapid decapitation of mice, 0.5-0.75 mL of trunk blood (blood immediately collected from the body at the site of decapitation) was collected, allowed to coagulate on ice for 30 min and centrifuged (15 min at 5,000 rpm). Serum (50 µL) was collected into fresh tubes followed by addition of ice cold 80% methanol (5× by volume), then stored at −80° C. overnight. On the next day, samples were centrifuged at 10,000 rpm for 15 min to eliminate methanol precipitated proteins. This methanol precipitation step was repeated and the metabolite containing supernatant was dried via speed-vacuum and stored at −80° C. until analysis.

Global, Untargeted UPLC-MS/MS Analysis

For mass spectrometry analysis, dried extracts were reconstituted in 100 µL of acetonitrile/water (80:20, v/v) and centrifuged for 5 min at 15,000 rpm to remove insoluble material. Quality control (QC) samples were prepared by pooling equal volumes from each experimental sample. Full MS (FMS) data was acquired for this QC pool, in both HILIC-POS (3 FMS QC runs) and HILIC-NEG (1 FMS QC runs) methods, to use as a retention time alignment reference within Progenesis QI for subsequent normalization and data quantitation. MS/MS (data dependent (DD)) acquisitions for pooled QCs were run to assess instrument performance over time and used for feature annotation (described below).

MS analyses were performed on a Q-Exactive HF hybrid mass spectrometer (Thermo Fisher Scientific, Bremen, Germany) equipped with a Vanquish UHPLC binary system and autosampler (Thermo Fisher Scientific, Germany). Extracts (5 uL injection volume) were separated on a SeQuant ZIC-HILIC 3.5-µm, 2.1 mm×100 mm column (Millipore Corporation, Darmstadt, Germany) held at 40° C. Liquid chromatography was performed at a 200 µL min-1 using solvent A (5 mM ammonium formate in 90% water, 10% acetonitrile) and solvent B (5 mM ammonium formate in 90% acetonitrile, 10% water) with the following gradient: 90% B for 2 min, 90-40% B over 16 min, 40% B held 2 min, and 40-90% B over 10 min, 90% B held 10 min (gradient length 40 min). Full MS analyses were acquired over a mass range of m/z 70-1050 under an ESI positive profile mode and separately under an ESI negative profile mode. Full mass scan was used at a resolution of 120,000 with a scan rate at ~3.5 Hz. The automatic gain control (AGC) target was set at 1×106 ions, and maximum ion injection time (IT) was at 100 ms. Source ionization parameters were optimized with the spray voltage at 3.0 kV, and other parameters were as follows: transfer temperature at 280° C.; S-Lens level at 40; heater temperature at 325° C.; Sheath gas at 40, Aux gas at 10, and sweep gas flow at 1. Data dependent (DD) MS/MS spectra were acquired using a data dependent scanning mode in which one full MS scan (m/z 70-1050) was followed by 2 MS/MS scans. MS/MS scans are acquired in profile mode using an isolation width of 1.3 m/z, stepped collision energy (NCE 20, 40, 60), and a dynamic exclusion of 6 s. MS/MS spectra were collected at a resolution of 15,000 with an AGC target set at 2×105 ions, and IT of 100 ms. To assess instrument performance and reproducibility throughout our experimental run sequence, the retention times and peak areas were determined for a subset of identified endogenous molecules (n=10) observed in the 3 DD QC pool runs bracketing the experimental FMS QC and experimental run sequence (visualized using Skyline (MacLean et al., Bioinformatics vol. 26, p. 966-968, 2010). These data demonstrate the reliability of the UPLC-MS/MS platform minimizing the importance of technical replicates.

Metabolite Data Processing and Analysis

UPLC-MS/MS raw data were imported, processed, normalized, and reviewed using Progenesis QI v.2.1 (Nonlinear Dynamics, Newcastle, UK). All FMS sample runs were aligned against a FMS QC pool reference, with alignment to the reference being ≥97%, demonstrating the reproducibility of the HILIC column separation method. Peak picking, with a minimum threshold of 250,000 ion intensity, was performed for individual aligned runs based on an aggregate run (representative of all ion peaks detected in all samples). Unique ions (retention time and m/z pairs) were grouped (a sum of the abundancies of unique ions) using both adduct and isotope deconvolutions to generate unique "features" (retention time and m/z pairs) representative of unannotated metabolites. Data were normalized to all features using Progenesis QI. Briefly, all runs have a measurement for every feature ion, therefore a ratio can be taken for the feature ion abundance in a particular run relative to the value in the normalization reference. Progenesis applies a Log 10 transformation to the ratio to yield a normal distribution on all ratio data within each run for all samples, and scalar estimations shift the Log 10 distributions onto that of the normalization reference. Resulting FMS data was utilized for relative quantitation. The minimum percent coefficient of variance (% CV) was determined for all features across sample groups. Data was exported to EZ Info (Umetrics Software) and unsupervised (% of mean) Principle Components Analysis (PCA) was used to visualize clustering of data groups (all features included) prior to statistical tests of significance. Additionally, within Progenesis QI, a one-way analysis of variance (ANOVA) test was used to assess significance between WT and KO groups and returned a P-value for each feature (retention time_m/z descriptor), with a nominal P-value ≤0.05 taken as significant. Significant features were further filtered using a fold change threshold calculated by Progenesis from combined abundance data, with a cutoff of FC≥|1.2| deemed as significant. Multiple testing correction (MTC) was conducted with Bioconductor's q-value package using the Storey method with the π0 method set to "bootstrap", a false discovery rate (FDR) level ≤0.1, and default parameters. Visualizations of dysregulated metabolites were represented by volcano plots (log 2 (fold change) vs. −log 10 (P-value)). Tentative and putative annotations were determined within Progenesis using accurate mass measurements (<5 ppm error), isotope distribution similarity, and manual assessment of fragmentation spectrum matching (when applicable) from the Human Metabolome Database (HMDB), Metlin, MassBank, and the National Institute of Standards and Technology (NIST) database. Additional putative annotations were assigned using Compound Discoverer 2.0 (Thermo Scientific, Waltham, Mass., USA). Briefly, the DDA data was uploaded to Compound Discoverer 2.0, deconvoluted to group isotopes/adducts of the same feature, and features were assigned an m/z Cloud spectral match score based on feature spectral matches against the mzCloud spectral libraries. For Level 3 confidence features (i.e., annotations supported by MS1 level data that may match multiple candidate annotations, including potential isomeric matches with indistinguishable chemical formula and spectral matches), mummichog 2.0 (Li et al., PLoS Comput Biol vol. 9, e1003123, 2013) was utilized to rank the most likely species within the samples. mummichog 2.0 predicts biological activity from MS1 data rather than formal manual curation of MS-2-dependent identifications. The MetaboAnalyst 3.0 program was used for pathway and metabolite set enrichment analyses using the list of statistical significance annotated features in the discovery dataset. KEGG metabolite pathways were visualized using Cytoscape 3.4.0 (The Cytoscape Consortium, USA). Increased confidence in the annotation of many features was achieved by manually assessing spectral match and RT consistencies between experimental data and chemical standards within a curated in-house library. Chemical standards (purchased from Sigma Aldrich (St. Louis, Mo.) unless otherwise specified) were prepared at a concentration of 10 ng/uL in acetonitrile/water (80/20, v/v).

Validation of Pathway Disruptions Via Metabolomic UPLC-MS/MS Analysis

UPLC-MS/MS raw data were imported, processed, normalized, and reviewed using Progenesis QI v.2.1 as described above for the initial discovery dataset with an additional pooled QC DD run acquired in the middle the sample injection sequence. After the raw data was imported and processed in Progenesis, mummichog 2.0 was used to perform pathway enrichment analysis by predicting biological activity from MS1 data allowing a focused assessment and validation of specific pathways sensitive to MBLAC1 KO. Significant pathways were determined using the Fisher exact test and corrected P-values were determined by modeling the raw P-values as a Gamma distribution and adjusted on the cumulative distribution function (CDF) of the Gamma model.

RESULTS

Generation and Validation of MBLAC1 KO Mice.

To eliminate expression of MBLAC1 in vivo and initiate a metabolomic interrogation of MBLAC1-linked pathways, a non-homologous end joining (NHEJ) CRISPR/Cas9 strategy was used to introduce deletions in the Mblac1 gene, disrupting sequences that encode the N-terminus of MBLAC1 protein as described in the Methods above (Hsu et al., Nat Biotechnol vol. 31, 827-832, 2013; Shen et al., Cell Res vol. 23, 720-723, 2013). This effort yielded two different deletion lines with either 5 bp or 14 bp deletions. The studies described in this report, derive solely from experiments with mice that harbor the 5 bp deletion, which lies 46 bp downstream of the MBLAC1 protein start site (FIG. 4A). The resulting frame shift results in the generation of 27 amino acids of ectopic sequence prior to strand termination (FIG. 4B). As shown in FIG. 4C, immunoblots of brain (cortical tissue) and liver extracts prepared from 5 bp deletion-containing KO mice, using affinity-purified MBLAC1 antibody, demonstrated complete loss of the 27 kDa band predicted to encode MBLAC1 protein (FIG. 4C) (see Example 1 above). The founder mouse, as well as subsequent heterozygous and homozygous KO progeny, were viable, produced offspring at normal Mendelian ratios (FIG. 4D), and exhibited no visible physical or behavioral abnormalities.

Figure 5:
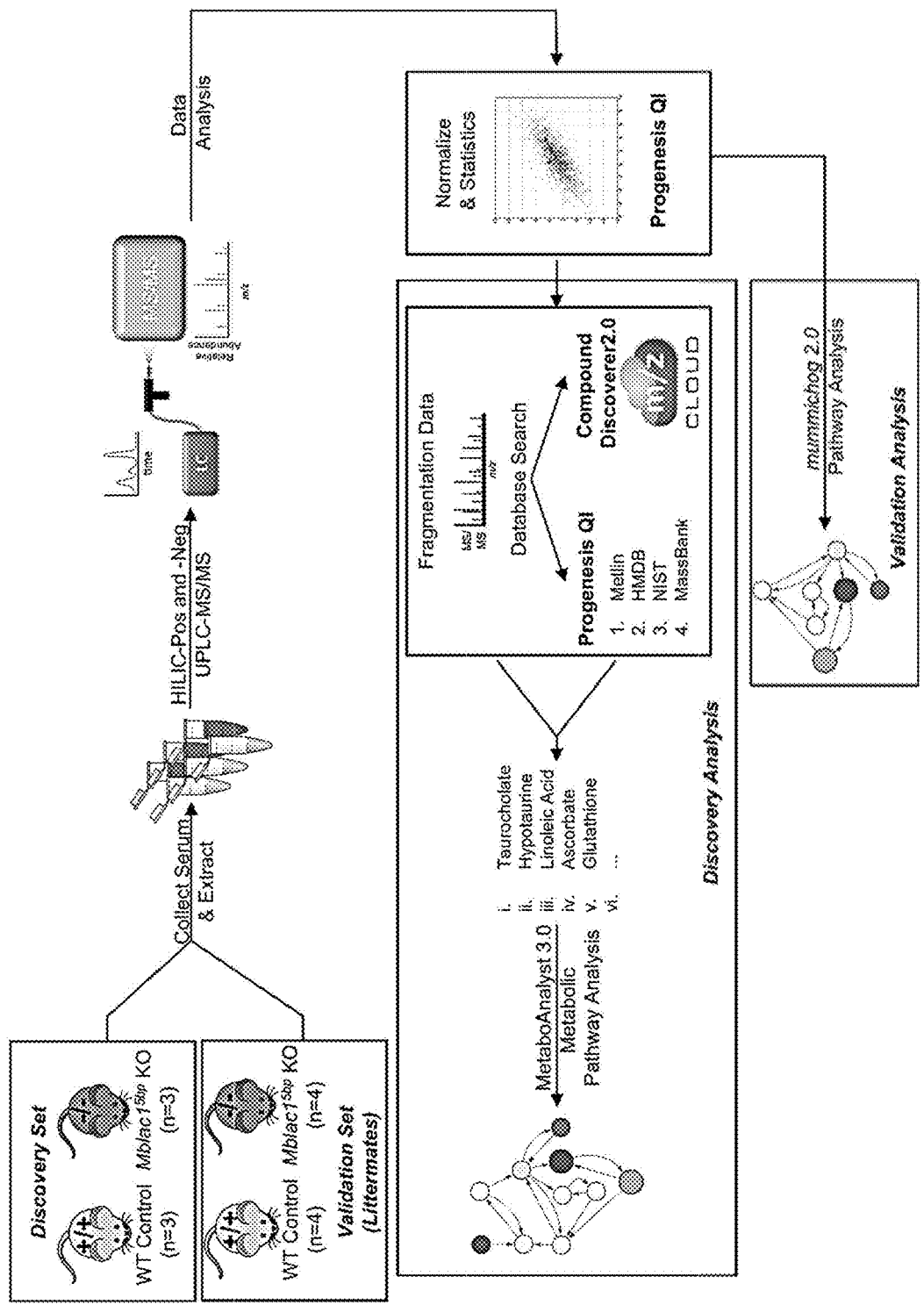
FIG. 5 is an illustration of the workflow for the global, untargeted MBLAC1 KO serum metabolomic discovery and validation studies. The workflow begins with serum sample preparation from age- and sex-matched controls for the discovery set, and serum sample preparation from littermate age- and sex-matched controls for the validation set. This diagram illustrates the steps required for the discovery-based analysis of a multidimensional dataset across several analysis platforms to curate tentative and putative feature annotations and prioritize metabolic pathways altered by loss of MBLAC1. Additionally, this illustration describes the validation analysis to identify replicable metabolic pathways sensitive to MBLAC1 loss.

The experimental design, from serum collection through data analysis, is depicted in FIG. 5. Serum samples were collected from WT and MBLAC1 KO mice and metabolites were separated by polarity using HILIC-POS and -Neg UPLC-MS/MS. For confidence in metabolite detection and putative identification of features, two complementary data processing and analysis platforms were pursued, Progenesis QI and Compound Discoverer 2.0 as described in Methods. Briefly, Progenesis QI was used for peak-picking, normalization and statistical analysis to determine uniqueness of MBLAC1 KO and WT sera metabolomes. Both Progenesis QI and Compound Discoverer 2.0 were used to assign annotations to features of interest based on database searches and spectral library matching. The compiled list of annotated, significantly regulated features was subsequently analyzed by MetaboAnalyst 3.0. where enrichment of known metabolic pathways was assessed. This approach was designed to identify metabolic pathways affected by loss of MBLAC1 expression, and thereby provide a physiological context for contributions of MBLAC1 substrate(s).

Elucidation of an MBLAC1-Dependent Serum Metabolome

UPLC-MS/MS methods are now commonly used for metabolomic studies owing to their high-resolution and sensitivity capabilities (Lin et al., J Proteome Res vol. 10, p. 1396-1405, 2011). As many endogenous metabolites found in serum samples are expected to be polar/hydrophilic, efforts were initiated using HILIC to retain and resolve polar analytes. Both HILIC-positive (POS) ion mode and HILIC-negative (NEG) ion mode MS methods were used to increase the molecular breadth of detected metabolites. Future studies may benefit from complementary reverse-phase liquid chromatography (RPLC)-MS methods. Representative total ion chromatograms for serum samples derived from WT and KO mice were produced. The Progenesis QI data processing platform was used, to inspect these runs for reproducible, genotype-dependent differences by normalizing to all feature abundances (each feature abundance is a sum of feature ion abundances comprised of grouped adduct forms). While not a direct indicator of efficacy, these analyses detected many molecular features (with unique mass to charge ratios (m/z)) in the data set, 2002 features in HILIC-POS and 2336 features in HILIC-NEG. Within Progenesis QI, feature sample variance is defined by the minimum percent coefficient of variance (min % CV) from any experimental group such that a low % CV value represents less abundance variance among biological samples. Based on other untargeted metabolomic studies, features with a min % CV ≤30% were considered as having acceptable abundance variation, with 69% of the features in HILIC-POS have a min % CV ≤30% and 57% of the features in HILIC-NEG have a min % CV ≤30%. The binning of features by min % CV ranges was determined. Subsequent, unsupervised PCA of these data revealed clear and consistent segregation of WT and KO biological replicates distinct from the pattern of pooled reference samples.

Next, a one-way ANOVA was used to nominate features that demonstrated genotype-dependent abundance differences between WT and KO samples, with a nominal P-value of ≤0.05 taken as significant. For HILIC-POS data, ANOVA analysis revealed 326 features as significant, 16% of the total number of features. For samples analyzed by HILIC-NEG, 287 features, 12% of the total, reached significance. In these discovery experiments, a liberal fold change [(FC) ≥|1.2|] was used as the filtering threshold, based on previous plasma metabolomics studies. Features significantly dysregulated between WT and KO samples from HILIC-POS and -NEG respectively were determined.

Nomination of Biomarkers of Loss of MBLAC1 Expression.

Metabolite identification was pursued for significant features, with a nominal P-value ≤0.05 and a FC ≥|1.2|. The experimental m/z measurement of each feature was queried against several published metabolite databases (i.e., HMDB, MassBank, Metlin, NIST, mzCloud) to match feature m/z within a ±5 ppm window. Various levels of confidence were assigned to the metabolite annotations (Table 1) based on the levels of metabolite identification first outlined by Sumner et al. 2007 and the Metabolomics Standard Initiative (Sumner et al., Metabolomics: Official Journal of the Metabolomic Society vol. 3, 211-221, 2007) and the more recent adaptations of this approach (representative suggested tentatively/putatively annotated features significantly sensitive to MBLAC1 loss from a discovery dataset). Several of the prioritized molecules do not match any current database entries, either representing novel metabolites (unknown unknowns) or unknown degradation or breakdown products that are absent from existing databases. These are classified most broadly as level 5 (L5) for a feature annotated with a unique m/z. A subset of the significantly regulated molecules in the data, classified as level 4 (L4), could be assigned multiple potential molecular formulas and thus render multiple candidate annotations. Level 3 (L3) features are classified based on a confident molecular formula and accurate mass. Tentative identifications were assigned to many L3 features by using mummichog 2.0 to predict the species found in the samples, and these putative annotations were denoted. Features are classified as level 2 (L2) when experimental fragmentation data is consistent with a spectral library match upon manual assessment and curation, rendering a putative. Pure reference standards generate match scores ranging from 20/100 to >99/100 against external spectral libraries. Thus, an arbitrary threshold of 45/100 was set to facilitate curation. A lower fragmentation score match was accepted for features with a low (<100) m/z that matched a single metabolite, in which case the low fragmentation score is likely a result of minimal fragmentation as well as potential MS/MS fragments being below the detection limit of the instrumentation platform. Together, Progenesis QI and Compound Discoverer 2.0 facilitated annotations for 16% (92 out of 593) of the significantly different features. The highest identification, confidence level (L1), is achieved by comparison of experimental data with that of a standard reference compound to confirm the structure with retention time, isotope pattern, and fragmentation.

TABLE 1

Initial Untargeted UPLC-MS/MS

| Pathway | Name | Formula | Mol. Wt. | Confidence level |
|---|---|---|---|---|
| Taurine and hypotaurine metabolism | Pyruvic acid** | C3H4O3 | 88.0160 | L3 |
| | L-alanine | C3H7NO2 | 89.0477 | L2 |
| | Taurine | C2H7NO3S | 125.0146 | L2 |
| | Hypotaurine↓ | C2H7NO2S | 109.0197 | L1 |
| | 3-Sulfinoalanine | C3H7NO4S | 153.0096 | L2 |
| | Taurohyocholic acid*/Taurocholic acid*↓ | C26H45NO7S | 515.2917 | L3 |
| | 2-Hydroxyethanesulfonate↓ | C2H6O4S | 125.9980 | L2 |
| Primary bile acid biosynthesis | Glycine | C2H5NO2 | 75.0320 | L1 |
| | Taurine | C2H7NO3S | 125.0144 | L2 |
| | Cholic acid | C24H40O5 | 408.2880 | L2 |
| | Chenodeoxycholic acid*/Deoxycholic acid* | C24H40O4 | 392.2927 | L3 |
| | Chenodeoxycholic acid*/Deoxycholic acid*↓ | C24H40O4 | 392.2927 | L3 |
| | Taurohyocholic acid*/Taurocholic acid*↓ | C26H45NO7S | 515.2917 | L3 |
| | Taurochenodeoxycholic acid↓ | C26H45NO6S | 499.2967 | L2 |
| Glutathione Metabolism | L-glutamate | C5H9NO4 | 147.0532 | L1 |
| | Glycine | C2H5NO2 | 75.0320 | L1 |
| | Ascorbic acid**↑ | C6H8O6 | 176.0321 | L2 |
| | Ornithine | C5H12N2O2 | 132.0899 | L2 |
| | gamma-L-Glutamyl-L-cysteine** | C8H14N2O5S | 250.0623 | L3 |
| | Pyroglutamic acid↓ | C5H7NO3 | 129.0426 | L2 |
| | Dehydroascorbic acid**↑ | C6H6O6 | 174.0164 | L3 |
| Linoleic acid metabolism | Linoleic acid↓ | C18H32O2 | 280.2402 | L2 |
| | 13(S)-HpODE | C18H32O4 | 312.0230 | L2 |
| | 13(S)-HODE*/9(10)-EpOME* | C18H32O3 | 296.2347 | L3 |
| | 13-OxoODE**↓ | C18H30O3 | 294.2195 | L3 |
| | 13(S)-HODE*/9(10)-EpOME* | C18H32O3 | 296.2347 | L3 |

*Isomeric metabolites cannot be differentiated in our data by MS2 or RT, thus both potential candidates are indicated and denoted as L3.
**L3 confidence level indicates that a feature has multiple candidate identification. Mummichog 2.0 was used to rank the most likely species which is denoted in table.
Metabolites of the identified pathways of interested to be confirmed and utilized for a future targeted MBLAC1 KO metabolomics studies. ID levels for each listed metabolite is based on the degree of confidence of putative identification (based on database identification and fragmentation data supporting ID) described in Sumner et al., 200745 and Schrimpe-Rutledge et al., 2016.33.
Those indicated with a downward arrow were downregulated in MBLAC1 KO mice, and those indicated with an upward arrow were upregulated in MBLAC1 KO mice.

Nomination of MBLAC1-Dependent Metabolic Pathways

To identify metabolic pathways altered by MBLAC1 KO, analysis with features of interest exhibiting moderate to high confidence levels of identification (L3-L1) was pursued. MetaboAnalyst 3.0 was used to map the 92 significantly dysregulated, putatively-identified metabolites to Kyoto Encyclopedia of Genes and Genomes (KEGG) defined pathways. After identifying the most dysregulated pathways, the total coverage of each pathway that was identified in the dataset was determined which allowed the increase of confidence in KEGG pathway assignment. HILIC-MS/MS provides effective retention, separation, and elution of polar molecules and consequently, lower representation of non-polar molecules is expected, and thus one would not expect to obtain full coverage of metabolic pathways. Several pathways, however, were identified as warranting further inspection, including taurine and hypotaurine metabolism, primary bile acid biosynthesis, glutathione metabolism, and linoleate metabolism.

The KEGG defined pathway for taurine and hypotaurine metabolism overlaps at multiple points with the pathway supporting primary bile acid homeostasis. The pathway intersection (containing 31 metabolites) is highlighted in a user-defined, hybrid "taurine, hypotaurine and primary bile acid metabolism" pathway with the highest (68%) coverage of metabolites in the dataset. Furthermore, 16% of the metabolites (i.e., 5 features) in this combined pathway are putatively identified as significantly reduced in KO samples (Table 1) with large fold changes (i.e. Taurochenodeoxycholic acid FC=|49.1|) observed, underscoring these pathways as particularly sensitive to the absence of MBLAC1 expression. Furthermore, the two linked pathways noted can also be associated with glutathione (GSH) metabolism. Thus, although no change was observed in cysteine, this amino acid is a key precursor to the synthesis of taurine related metabolites and is also a key amino acid in the GSH pathway, which MetaboAnalyst 3.0 KEGG pathway analysis revealed to be significantly impacted by loss of MBLAC1 expression, with 8% (3 features) of KEGG GSH metabolites altered in KO serum (Table 1). Lastly, the MetaboAnalyst 3.0 KEGG pathway analysis identified linoleate metabolism as a pathway with changes in a sizeable number of metabolites detected (40% total metabolic pathway coverage and identified to have 13% over-representation of significantly dysregulated metabolites). Together these findings encouraged a follow up experiment of MBLAC1 KO metabolic changes, in comparison to MBLAC1 WT, to validate the impact of the MBLAC1 KO, with particular reference to the metabolic pathways highlighted above (pathways of interest).

Validation of Metabolic Pathway Disruptions Induced by Loss of MBLAC1

Using an independent set of serum samples prepared from four age- and sex-matched (female) littermate MBLAC1 KO and four WT mice, follow-up metabolic pathway based analyses were conducted to provide preliminary validation of MBLAC1 sensitive metabolic pathways determined from the initial age and sex-matched, but non-littermate derived serum samples (FIG. 5). The validation dataset corroborated the presence of 80% (19/24) of the unique features putatively identified in pathways of interest (Table 1) in the discovery set of serum samples by Progenesis QI, though some features were not detected. Utilizing the second set of serum samples to pursue validation of the discovery dataset at the specific pathway level, mummichog 2.0, was again used to determine the metabolic pathways impacted by loss of MBLAC1 (FIG. 5). The software predicted bile acid biosynthesis (P-value=0.042, 5 significant features out of 18 pathway features) and linoleate metabolism (P-value=0.0002, 7 significant features out of 14 pathway features), reproducing two of the pathways from the initial discovery findings that the top metabolic pathways affected by loss of MBLAC1 include primary bile acid biosynthesis and linoleate metabolism. Multiple other pathways were nominated as significantly impacted by MBLAC1 KO, though almost all of these derive from 2-3 molecules within their designated network. A notable exception is a pathway linked to urea cycle/amine group metabolism, where 9 of 38 features were nominated, though this pathway had not been identified in the earlier discovery analysis. In the validation analysis, a significant perturbation of GSH metabolism following loss of MBLAC1 was not identified. As the bile acid synthesis pathway, which retained significance, shares molecules with that of the GSH metabolic pathway, the lack of significance of the latter network may reflect an overall weaker effect of MBLAC1 genotype that becomes insignificant in the context of the more stringent, littermate based design of the validation experiment. Alternatively, this difference could derive from unknown variables associated with animal housing and husbandry at the two sites where samples were derived.

Potential Significance of Perturbation of Taurine-Derived Metabolites within the Primary Bile Acid Biosynthesis Pathway As noted above, MBLAC1 KO appears to result in a consistent reduction in the abundance of many taurine derived metabolites such as taurochenodeoxycholic acid and taurocholate that reside in the primary bile acid metabolism pathway. Indeed, these features represent the most significantly altered and putatively identified metabolites in the dataset, with the greatest magnitude of change due to loss of MBLAC1. This pathway validation data provided additional support for bile acid biosynthesis and taurine derived metabolites as highly sensitive to MBLAC1 expression. Taurine and related metabolites have many important biological roles, ranging from essential contributions to bile acid conjugation in the liver, to the regulation of cardiac and skeletal muscle function, and evidence suggests that they can cross the blood brain barrier and regulate neurotransmission. Taurine has been shown to be protective against oxidative stress induced cell death in peripheral tissues such as liver in several animal models of hepatotoxicity. Likewise, tauroursodeoxycholic acid (TUDCA), a bile acid derivative of taurine, has been shown to be neuroprotective in in vitro and in vivo models of cell death such as retinal degeneration where the compound has been found to markedly decrease retinal neural cell death by reducing cellular stress and preventing release of pro-apoptotic factors. Therefore, loss of these molecules from the serum of MBLAC1 KO mice may indicate a role played by the MBLAC1 substrate in triggering the induction of taurine metabolic pathways that protect against cell stress and cell death. Chronic Cef treatment of cells has previously been reported to act via a Nrf2 pathway to induce expression of the cysteine/Glu exchanger and the Na+-dependent Glu transporters that can diminish the threat of excitotoxic insults and oxidative stress. It is hypothesized that short term Cef blockade of MBLAC1 is detected as a stressful event by Nrf2, whereas the lifelong absence of MBLAC1 may preclude cells from mounting an appropriate stress response, as revealed in a reduction in bile acid pathway molecules in the serum of MBLAC1 KO mice.

Potential Significance of Alterations in Linoleate Metabolism

In the validation analysis, it was confirmed that linoleate metabolism is one of the metabolic pathways sensitive to loss of MBLAC1. Linoleic acid is an essential poly-unsaturated, omega-6 fatty acid (PUFA) primarily known as a precursor for the biosynthesis of arachidonic acid. Alterations in linoleic acid levels have been associated with a wide variety of health consequences ranging from perturbations of skin and hair health, as well as obesity and cardiovascular disease. As changes in the metabolites of the linoleic acid metabolism pathway in MBLAC1 KO mice were observed, it is hypothesized that MBLAC1 KO mice may be more susceptible to abnormal brain health, a hypothesis that can be assessed through disease-mimicking pharmacological and genetic challenges.

Summary

Using an unbiased metabolomic approach, based on an UPLC-MS/MS, serum metabolome changes arising from constitutive elimination of MBLAC1, an enzyme of as yet undetermined function, were evaluated. Ninety-two annotations were assigned to features of interest that significantly differed in abundance in the serum of MBLAC1 KO mice compared to WT controls. MetaboAnalyst 3.0 and KEGG pathway analysis nominated multiple metabolic pathways impacted in the KO, with several linked to neuroprotective, oxidative stress reducing pathways. In an independent validation study, an impact of loss of MBLAC1 on bile acid biosynthesis and linoleate metabolism, pathways that share cell protective actions in the face of metabolic and oxidative cellular stress, was confirmed. These studies designate metabolic pathways that should be pursued in future, targeted analyses and that may ultimately reveal the endogenous substrate(s) for MBLAC1/SWIP-10. These are networks identified in serum, however, other networks can be identified through similar approaches in urine, tissues or brain fluid or regions, for example. The reported neuroprotective actions of Cef, a demonstrated MBLAC1 ligand, may derive from the induction of cell defense mechanisms such as those designed to limit oxidative stress, effects that cannot be sustained in the context of a full loss of the enzyme.

Example 3—Effect of Repeated Cef on Cocaine-Induced Locomotion

Methods:

Animals: All mice were used in accordance with protocols approved by the Florida Atlantic University Institutional Animal Care and Use Committee. Mice were group-housed on a 12 h/12 h light/dark cycle and given ad libitum access to food and water. Breeding was accomplished with mating of heterozygous males with heterozygous females. Male and female mice 11-13 weeks old at the start of the experiment were used in testing the effects of repeated ceftriaxone on response to cocaine in the open field assay. Data from males and females were combined.

Repeated Cef treatment/acute cocaine administration: MBLAC1 wild-type (WT, MBLAC1$^{+/+}$) and knockout mice (MBLAC1$^{-/-}$) were used in this experiment. Mice were injected IP once daily for 10 days with 200 mg/kg ceftriaxone (CEF) or saline. Twenty-four hours following the last CEF injection, mice were injected with 10 mg/kg cocaine or saline followed immediately by testing in open field activity chambers (Med Associates, Fairfax, Vt.) for 60 minutes. Locomotor activity was evaluated by photocells in the X, Y and Z dimensions. Horizontal beam breaks, vertical beam breaks, and repetitive movements were recorded and measures, including distance traveled, vertical rearing and stereotypic counts, were calculated. Data were analyzed in 5 min time bins within session, and for the first 30 min following cocaine injection. Data were analyzed by two-way ANOVA repeated measures, with time bin as the repeated measure, or by two-way ANOVA for 30 min cumulated data. At the end of behavior, mice were euthanized by $CO_2$.

The methods were performed essentially as described in Tallarida et al. Neurosci Lett vol. 556, p. 155-159, 2013.

Figure 6:
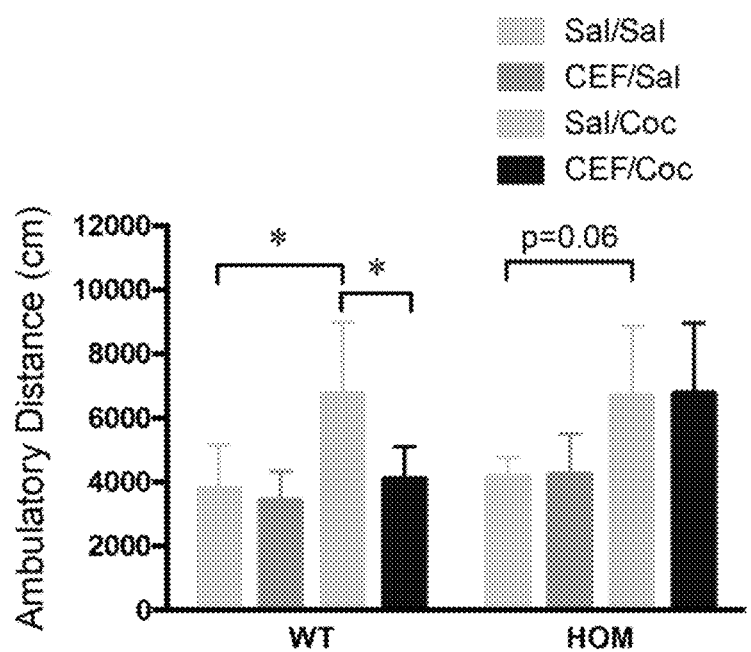
FIG. 6 is a graph showing the effect of repeated Cef on cocaine-induced locomotion. Mice were injected IP once daily for 10 days with 200 mg/kg CEF or vehicle. Twenty-four hours following the last Cef injection, mice were injected with 10 mg/kg cocaine or vehicle followed immediately by testing in open field activity chambers for 60 minutes. Distance travelled (cm) in the first 30 min following cocaine injection was calculated and data are expressed as the mean+/−SEM for each group. *p<0.05, Student's t-test. CEF, ceftriaxone; COC, cocaine, HOM, homozygote; WT, wild-type.

Results:

MBLAC1 WT and MBLAC1 KO mice responded to cocaine with an increase in total ambulatory distance in the open field in the first 30 min of a 60 min session compared to mice injected with saline (FIG. 6). Ten days of pretreatment with CEF completely blocked the effects of cocaine on MBLAC1 WT mice. However, the repeated CEF treatment had no effect on the response to cocaine in MBLAC1 KO mice.

Example 4—Cocaine Sensitization

Methods:

Animals: All mice were used in accordance with protocols approved by the Florida Atlantic University Institutional Animal Care and Use Committee. Mice were group-housed on a 12 h/12 h light/dark cycle and given ad libitum access to food and water. Breeding was accomplished with mating of heterozygous males with heterozygous females. Male and female mice 11-13 weeks old at the start of the experiment were used in testing the effects of repeated cocaine in the open field assay. Data from males and females were combined.

Repeated cocaine administration: Mblac1 wild-type (WT, Mblac1$^{+/+}$) and knockout (KO) mice (HOM, Mblac1$^{-/-}$) were used in this experiment. On day 1, mice were placed in the open field activity chambers (Med Associates, Fairfax, Vt.) for 30 min as a habituation. On day 2, no behavior was performed. On day 3, mice were placed in the open field for 30 min, removed and administered a saline injection, and placed back in the open field for 60 min. On day 4, no behavior was performed. On day 5-9, mice were placed in the open field for 30 min, removed and administered 10 mg/kg cocaine, IP, and placed back in the open field for 60 min. Then, on day 10, mice were placed in the open field for 30 min, removed and administered a saline injection, and placed back in the open field for 60 min. This was followed by a two-week abstinence period during which mice receive no treatments. This was followed by a single day on which mice are placed in the open field for 30 min, removed and administered a cocaine injection, and placed back in the open field for 60 min. At the end of behavior, mice were euthanized by $CO_2$. Locomotor activity was evaluated by photocells in the X, Y and Z dimensions. Horizontal beam breaks, vertical beam breaks, and repetitive movements were recorded and measures, including distance traveled, vertical rearing and stereotypic counts, were calculated. Data were analyzed in 5 min time bins within session, and for the 60 min following cocaine injection. Data were analyzed by two-way ANOVA repeated measures, with time bin as the repeated measure, or by two-way ANOVA for 60 min cumulative data. At the end of behavior, mice were euthanized by $CO_2$.

Figure 7A:
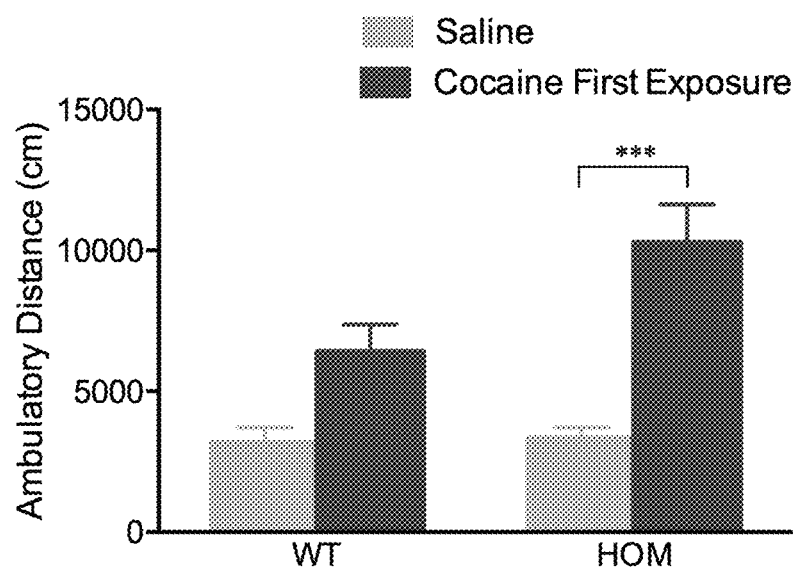
FIGS. 7A and 7B are a pair of graphs showing the effect of repeated cocaine on open field activity. HOM mice demonstrate an enhanced response to the effects of cocaine, and an increased development of cocaine-induced sensitization. Mice were injected with 10 mg/kg cocaine for five consecutive days, and once two weeks later, followed immediately after each injection by recording of activity in open field activity chambers for 60 minutes. Ambulatory distance travelled (cm) in the total 60 min period following cocaine injection was calculated and data are expressed as the mean+/−SEM for each group. *p<0.05, *p<0.001, **p<0.0001, Tukey's multiple comparisons test. HOM, homozygote; WT, wild-type.
Figure 7B:
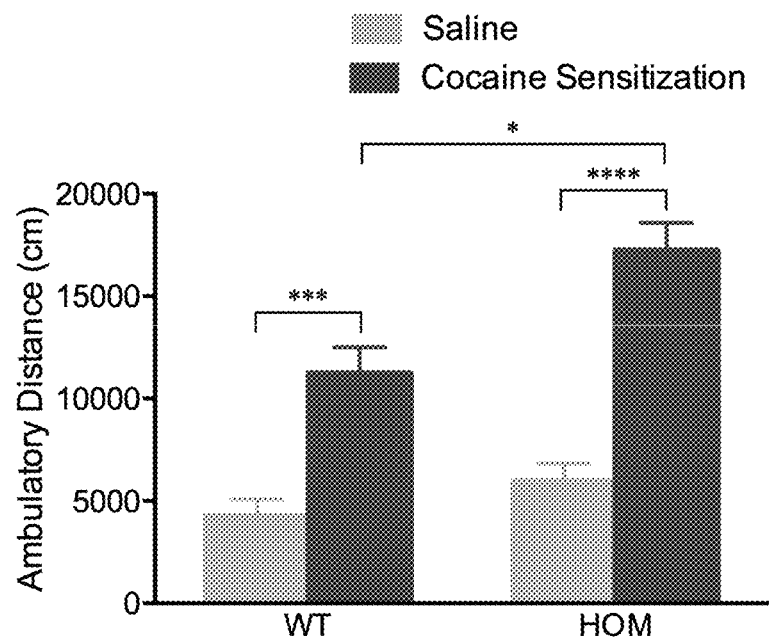

Results:

On the first day of cocaine administration, MBLAC1 HOM mice responded to cocaine with an increase in total ambulatory distance in the open field compared to mice injected with saline (FIG. 7A). The effect of cocaine on activity in MBLAC1 WT mice was not significant, suggesting that HOM are more sensitive to cocaine than WT mice (FIG. 7A). Two weeks later, a single injection of cocaine resulted in increased open field activity in both WT and HOM mice; however, the increase in activity was greater in HOM compared to WT mice (FIG. 7B). Furthermore, the cocaine-induced open field activity after two weeks was greater in HOM compared to the effect on day of cocaine for this group, whereas this was not different for WT mice. Thus, HOM mice demonstrate a sensitized effect of cocaine at two weeks that was not observed in WT. Taken together, these data support an enhanced response of HOM mice to the effects of cocaine, and an increased development of sensitization.

Other Embodiments

Any improvement may be made in part or all of the method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method for identifying therapeutic agents for treatment of addiction to a substance of abuse that require MBLAC1 to reduce actions of the substance of abuse, the method comprising the steps of:
   (a) providing at least one test agent, MBLAC1 protein or MBLAC1-expressing cells, and Ceftriaxone (Cef); and
   (b) using an assay to determine whether the at least one test agent is capable of disrupting binding between MBLAC1 protein and Cef, wherein a test agent capable of disrupting binding between MBLAC1 protein and Cef is identified as a candidate therapeutic agent for treatment of addiction to a substance of abuse; and ((c) administering the candidate therapeutic agent and the substance of abuse to at least one MBLAC1 knock-out (KO) animal and to at least one wild-type (WT) MBLAC1 animal and subsequently subjecting the animals to at least one test selected from the group consisting of: a locomotor assay, a withdrawal assay, a sensitization assay, consisting of: a locomotor assay, a self-administration assay, a reinstatement to drug assay, an analysis of white matter changes, and an analysis of changes in GLTI expression,
   wherein if the candidate therapeutic agent reduces or eliminates the actions of the substance of abuse in the WT MBLAC1 animal but not in the MBLAC1 KO animal, the candidate therapeutic agent is a therapeutic agent that requires the presence of MBLAC1 to reduce actions of a substance of abuse.

2. The method of claim 1, wherein the test agent is capable of disrupting binding between MBLAC1 protein and Cef and/or binds to MBLAC1 protein with an affinity of $K_D=2$ μM or less.

3. The method of claim 1, wherein the substance of abuse is selected from the group consisting of: cocaine, amphetamine, morphine, ethanol, methamphetamine, clorazepate, cathinones, bath salts, heroin, nicotine, alcohol, ketamine, and MDMA.

4. The method of claim 1, wherein the MBLAC1 protein is human MBLAC1 protein.

5. The method of claim 1, wherein the at least one test agent is a β-lactam antibiotic.

6. The method of claim 1, wherein a library of test agents comprises the at least one test agent.

7. The method of claim 6, wherein the library consists essentially of β-lactam structures.

8. The method of claim 6, wherein the library is an organic molecule library or a peptide library.

9. The method of claim 1, wherein the assay of step (b) is selected from the group consisting of: microcalorimetry, surface plasmon resonance, backscattering interferometry, radioligand binding assay, and an assay that can detect binding of unlabeled small molecules and proteins.

10. The method of claim 1, wherein the animals are rodents.

* * * * *

SEQUENCE LISTING

<160> NUMBER OF SEQ ID NOS: 13

<210> SEQ ID NO 1
<211> LENGTH: 266
<212> TYPE: PRT

<213> ORGANISM: HOMO SAPIENS

<400> SEQUENCE: 1

```
Met Arg Thr Glu Pro Leu Cys Gly Ala Ser Pro Leu Leu Val Pro Gly
1               5                   10                  15
Asp Pro Tyr Ser Val Val Leu Leu Gln Gly Tyr Ala Glu Pro Glu
            20                  25                  30
Gly Val Gly Asp Ala Val Arg Ala Asp Gly Ser Val Thr Leu Val Leu
        35                  40                  45
Pro Gln Thr Arg Gly Pro Ala Ser Ser His Arg Glu Ser Pro Arg Gly
    50                  55                  60
Ser Gly Gly Ala Glu Ala Ala Leu Glu Glu Ala Arg Gly Pro Ile
65                  70                  75                  80
Leu Val Asp Thr Gly Gly Pro Trp Ala Arg Glu Ala Leu Leu Gly Ala
                85                  90                  95
Leu Ala Gly Gln Gly Val Ala Pro Gly Asp Val Thr Leu Val Val Gly
            100                 105                 110
Thr His Gly His Ser Asp His Ile Gly Asn Leu Gly Leu Phe Pro Gly
        115                 120                 125
Ala Ala Leu Leu Val Ser His Asp Phe Cys Leu Pro Gly Gly Arg Tyr
    130                 135                 140
Leu Pro His Gly Leu Gly Glu Gly Gln Pro Leu Arg Leu Gly Pro Gly
145                 150                 155                 160
Leu Glu Val Trp Ala Thr Pro Gly His Gly Gly Gln Arg Asp Val Ser
                165                 170                 175
Val Val Val Ala Gly Thr Ala Leu Gly Thr Val Val Ala Gly Asp
            180                 185                 190
Val Phe Glu Arg Asp Gly Asp Glu Asp Ser Trp Gln Ala Leu Ser Glu
        195                 200                 205
Asp Pro Ala Ala Gln Glu Arg Ser Arg Lys Arg Val Leu Val Val Ala
    210                 215                 220
Asp Val Val Pro Gly His Gly Pro Pro Phe Arg Val Leu Arg Glu
225                 230                 235                 240
Ala Ser Gln Pro Glu Thr Glu Gly Gly Gly Asn Ser Gln Gln Glu Pro
                245                 250                 255
Val Val Gly Asp Glu Glu Pro Ala Leu His
            260                 265
```

<210> SEQ ID NO 2
<211> LENGTH: 2031
<212> TYPE: DNA
<213> ORGANISM: HOMO SAPIENS

<400> SEQUENCE: 2

```
agatactcgg gacgctgagg cgggaggatc acatgagccc aggaggttga ggctgcagtg    60
aggtatgatc gcgccactgc actcctgcct gggcaactga gcatgaaccc tcctcaaagc   120
taatggcgct tcaaaattct gcagtgcaaa gaagttgctg gggttgcgga gcggagaacc   180
gccaggaggc tggagcccag ccaggcagcc tcctcgggca cacggtgaag gcgccggaac   240
tacagctacc tccgcggcgc cgcttcggcc gccatatctg ggtacacggg aaccgcagag   300
gacaaactct cacccgcgtt ttcgatttct gcgctttctt cgagtgaggc aagacctagc   360
agaggcccaa ggtagagcgc ggctaggatt cgatggaggg aaacataaag gatagccttt   420
ggagggtgac gggcaaggac gtacgtaccg cgaacggaat ggggcggggg ccgaggacgc   480
```

-continued

```
cgagggaggg gcgggcccaa gtgtgaaggg agtctgggcg ataccatttt gggcaggggt       540
tgagggtgat accaacttaa tgggaggcgg gtggcagaga accgaggctt aggggcagtg       600
gcggggccga gcgcgggtgg gggatcgcgg agggacagga cggtcgccca ctgctccatt       660
tcctttctcc ccagcccgtc cctccctgcc aggagcagcc tcatgcggac cgagccgctg       720 tgcgggcat  cccctctgct ggtgcccggc gaccccatact ctgtggtggt tctgctgcag      780
ggctacgcgg agccagaggg tgtgggcgat gccgtgcgcg ccgacggctc cgtgaccctg       840
gtcctacccc agacccgggg cccggcctcc agccaccgag agtccccgcg cgggagtggc       900
ggcgcagagg ccgccctgga ggaggcgcc  cgtggcccca tcctggtgga caccgggggc       960
ccctgggctc gggaggcgct gctggggggcg ctggcggggc agggcgtggc cccgggagac     1020
gtgacgctag tggtggggac ccacgggcac tcggatcaca tcgggaactt ggggctgttc      1080 ccagcgcgg  ctctgctggt ctcgcacgac ttctgccttc ccggaggccg ctacctgccc      1140
cacgggctgg gtgaggggca gcccctgcgc ctgggcccgg ggctcgaggt gtgggccacg      1200
ccgggccacg ggggccagcg cgacgtgagc gtggtggtgg ccggcacggc tctgggcacc      1260
gtggtggtgg cgggagatgt gtttgagcga gatgggggacg aggattcgtg gcaggcactg     1320
agtgaagacc ccgcagccca ggagcggagc cggaagaggg tcctggtcgt tgccgacgtg      1380
gtcgtacctg gtcacgggcc ccccttttcga gtgttaaggg aagcctcgca gcccgagacg     1440
gagggtggag ggaacagcca gcaggagccg gtggtcggag acgaggagcc cgccctgcac      1500
taatcagcct cgagagggac tgcactcttg tcagggaagc cctaacagcg aagagctgct      1560
ggagacagag tcagagcagt caagggtggg agcttccagc ccttccagga ggccagtttt      1620
ctagtgaaga cagagtgcac ctgacactgc catcacatcg tcagtatcac tgcctgtctc      1680
tgccaccaaa ctaagatcaa aggagggggct cagctccctg tgcattctcc ctgggcctca    1740
gtaaaatggg agaaggttcg tgggagggggc ctccaaaata aaatggaaa ctgcattgaa      1800 aatcatagtg ccctagtgta aatgtgaagc attgacaatg ataatcgtgc aaacatggta      1860
atctacaact acagcagagg catactttgg ccaattgccc ctttcttata ggatggaggt      1920
tgctgagaga aggtacaggg cataaagatg accccttagt cacctgactt atgtatttgt      1980
tcatattttt ttgtcacaca ggctagagtg cagttgtgca gtcatagctc a              2031
```

<210> SEQ ID NO 3
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 3

```
ggaaacgacc gcaggtcgcc g                                                  21
```

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 4

```
gacagcgata gtttagtttc                                                    20
```

<210> SEQ ID NO 5
<211> LENGTH: 18

```
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 5
ttgctggcgt ccagcggc                                              18

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 6
gacagcgata gtttagtttc                                            20

<210> SEQ ID NO 7
<211> LENGTH: 18
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 7
tccctggcgt ccagcggc                                              18

<210> SEQ ID NO 8
<211> LENGTH: 16
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 8
cgagcccctg catcct                                                16

<210> SEQ ID NO 9
<211> LENGTH: 15
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 9
gccgcgcagc agaac                                                 15

<210> SEQ ID NO 10
<211> LENGTH: 71
<212> TYPE: DNA
<213> ORGANISM: MUS MUSCULUS

<400> SEQUENCE: 10
atgaacggtc cagtgcgcac cgagcccctg catggtgaga tcccctttgct ggcgtccagc   60 ggctcctact c                                                     71

<210> SEQ ID NO 11
<211> LENGTH: 71
<212> TYPE: DNA
<213> ORGANISM: MUS MUSCULUS
```

```
<400> SEQUENCE: 11
tacttgccag gtcacgcgtg gctcggggac gtaccactct agggaaacga ccgcaggtcg    60
ccgaggatca g                                                         71

<210> SEQ ID NO 12
<211> LENGTH: 43
<212> TYPE: PRT
<213> ORGANISM: MUS MUSCULUS

<400> SEQUENCE: 12

Met Asn Gly Pro Val Arg Thr Glu Pro Leu His Gly Glu Ile Pro Leu
1               5                   10                  15

Leu Ala Ser Ser Gly Ser Tyr Ser Val Val Leu Leu Arg Gly Tyr
            20                  25                  30

Ala Glu Pro Gln Gly Ala Gly Asp Ala Val Arg
        35                  40

<210> SEQ ID NO 13
<211> LENGTH: 42
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 13

Met Asn Gly Pro Val Arg Thr Glu Pro Leu His Gly Glu Ile Pro Gly
1               5                   10                  15

Val Gln Arg Leu Leu Leu Arg Gly Gly Ser Ala Ala Arg Leu Arg Gly
            20                  25                  30

Ala Ala Gly Ser Gly Arg Arg Gly Ala Cys
        35                  40
```